(12) United States Patent
McLaughlin et al.

(10) Patent No.: US 12,350,372 B2
(45) Date of Patent: *Jul. 8, 2025

(54) MINIMIZING AGGLOMERATION OF DRUG PARTICLE COATING MATERIAL DURING STORAGE TO STABILIZE DISINTEGRATION TIMES OF PHARMACEUTICAL PRODUCTS

(71) Applicant: Catalent U.K. Swindon Zydis Limited, Glasgow (GB)

(72) Inventors: Rosaleen McLaughlin, Swindon (GB); Simon Andrew Martyn Howes, Swindon (GB); Craig Wheadon, Swindon (GB); Jonathon Whitehouse, Herne Bay (GB)

(73) Assignee: Catalent U.K. Swindon Zydis Limited, Glasgow (GB)

( * ) Notice: Subject to any disclaimer, the term of this patent is extended or adjusted under 35 U.S.C. 154(b) by 55 days.

This patent is subject to a terminal disclaimer.

(21) Appl. No.: 18/451,593

(22) Filed: Aug. 17, 2023

(65) Prior Publication Data
US 2023/0390205 A1 Dec. 7, 2023

Related U.S. Application Data

(60) Continuation of application No. 17/307,638, filed on May 4, 2021, now Pat. No. 11,779,540, which is a
(Continued)

(51) Int. Cl.
*A61K 9/14* (2006.01)
*A61K 9/16* (2006.01)
(Continued)

(52) U.S. Cl.
CPC ............ *A61K 9/167* (2013.01); *A61K 9/1623* (2013.01); *A61K 9/1652* (2013.01); *A61K 9/1658* (2013.01)

(58) Field of Classification Search
CPC .... A61K 9/167; A61K 9/1623; A61K 9/1652; A61K 9/1658; A61K 9/0056;
(Continued)

(56) References Cited

U.S. PATENT DOCUMENTS

| 4,305,502 A | 12/1981 | Gregory et al. |
| 4,371,516 A | 2/1983 | Gregory et al. |

(Continued)

FOREIGN PATENT DOCUMENTS

| CA | 2398288 A1 | 8/2001 |
| CA | 2512988 A1 | 8/2004 |

(Continued)

OTHER PUBLICATIONS

Andrews. (2017)."How to Extract Oil from Orange Peels," downloaded from URL https://web.archive.org/web/20170603094953/https://www.wikihow.com/Extract-Oil-from-Orange-Peels retrieved on May 24, 2023; 5 pages.
(Continued)

*Primary Examiner* — Ernst V Arnold
(74) *Attorney, Agent, or Firm* — Morrison & Foerster LLP

(57) ABSTRACT

Provided are pharmaceutical compositions and methods for preparing pharmaceutical compositions using solventless mixing methods. Excess coating material that is not bound to a coated API particle may be removed by a sieving process. Coating and dosing ratios can also be optimized to minimize the amount of excess unbound coating material. Specifically, a coating ratio and/or a dosing ratio can be used to minimize the residual amount of excess unbound coating material to minimize agglomeration of coating material during storage. In some embodiments, a pharmaceutical composition is provided, the pharmaceutical composition comprising: 65-85% w/w API particles; 15-30% w/w coat-
(Continued)

ing material coating the API particles; and 3-15% w/w matrix surrounding the coated API particles, wherein the pharmaceutical composition comprises a disintegration time rate of less than 10 seconds for at least six months under storage conditions of at least 25° C. and at least 60% relative humidity.

15 Claims, 11 Drawing Sheets

Related U.S. Application Data division of application No. 17/008,318, filed on Aug. 31, 2020, now Pat. No. 11,026,892, which is a continuation of application No. 16/797,927, filed on Feb. 21, 2020, now Pat. No. 11,141,380.

(60) Provisional application No. 62/809,307, filed on Feb. 22, 2019.

(51) Int. Cl.
*A61K 9/50* (2006.01)
*A61P 29/00* (2006.01)

(58) Field of Classification Search
CPC .. A61K 9/2095; A61K 31/192; A61K 9/5063; A61K 9/0053; A61K 9/19; A61K 9/2813; A61K 9/282; A61K 9/284; A61K 9/2886; A61K 9/5073; A61K 47/02; A61K 47/44; A61K 9/2081; A61K 9/2018; A61K 9/205; A61K 9/2063; A61K 9/501; A61K 9/5015; A61K 9/14; A61K 9/141; A61K 9/50; A61P 29/00
See application file for complete search history.

(56) References Cited

U.S. PATENT DOCUMENTS

| | | | |
|---|---|---|---|
| 4,758,598 A | 7/1988 | Gregory | |
| 5,008,117 A | 4/1991 | Calanchi et al. | |
| 5,320,848 A | 6/1994 | Geyer | |
| 5,558,880 A | 9/1996 | Gole et al. | |
| 5,976,577 A | 11/1999 | Green et al. | |
| 6,214,386 B1 | 4/2001 | Santus | |
| 6,413,549 B2 | 7/2002 | Green et al. | |
| 6,509,040 B1 | 1/2003 | Murray et al. | |
| 6,709,669 B1 | 3/2004 | Murray et al. | |
| 6,951,657 B1 | 10/2005 | Zuccarelli | |
| 9,107,851 B2 | 8/2015 | Dave et al. | |
| 11,026,892 B2* | 6/2021 | McLaughlin | A61K 9/0056 |
| 11,077,067 B2* | 8/2021 | McLaughlin | A61K 47/44 |
| 11,141,380 B2* | 10/2021 | McLaughlin | A61K 9/0056 |
| 11,166,919 B2* | 11/2021 | McLaughlin | A61K 9/501 |
| 11,185,508 B2* | 11/2021 | McLaughlin | A61K 9/288 |
| 11,779,540 B2* | 10/2023 | McLaughlin | A61K 9/5063 |
| | | | 424/498 |
| 2003/0185096 A1 | 10/2003 | Hollstein et al. | |
| 2003/0195179 A1 | 10/2003 | Sawa | |
| 2004/0137061 A1 | 7/2004 | Ishibashi et al. | |
| 2004/0170686 A1 | 9/2004 | Fredrickson et al. | |
| 2004/0265373 A1 | 12/2004 | Wynn et al. | |
| 2007/0148099 A1 | 6/2007 | Burke et al. | |
| 2007/0292508 A1 | 12/2007 | Szamosi et al. | |
| 2008/0075825 A1 | 3/2008 | Fuisz et al. | |
| 2008/0096979 A1 | 4/2008 | Pilgaonkar | |
| 2008/0113021 A1 | 5/2008 | Shen | |
| 2008/0311201 A1 | 12/2008 | Der-Yang et al. | |
| 2008/0317853 A1 | 12/2008 | Kashid et al. | |
| 2009/0062241 A1 | 3/2009 | Bauer | |
| 2009/0148524 A1 | 6/2009 | Higuchi et al. | |
| 2011/0229573 A1 | 9/2011 | Tian | |
| 2014/0105936 A1 | 4/2014 | Limonov et al. | |
| 2014/0106059 A1 | 4/2014 | Dave et al. | |
| 2016/0361335 A1 | 12/2016 | Jacob et al. | |
| 2020/0268667 A1 | 8/2020 | McLaughlin et al. | |
| 2020/0268668 A1 | 8/2020 | McLaughlin et al. | |
| 2020/0268676 A1 | 8/2020 | McLaughlin et al. | |
| 2020/0268677 A1 | 8/2020 | McLaughlin et al. | |

FOREIGN PATENT DOCUMENTS

| | | | |
|---|---|---|---|
| CN | 102300558 A | 12/2011 | |
| CN | 102579390 A | 7/2012 | |
| CN | 103169655 A | 6/2013 | |
| CN | 104853751 A | 8/2015 | |
| EP | 0636365 A1 * | 2/1995 | ............... A61K 9/20 |
| EP | 1405635 A1 | 4/2004 | |
| EP | 1621186 A1 | 2/2006 | |
| GB | 211423 A | 2/1924 | |
| GB | 1548022 A | 7/1979 | |
| JP | H9-511256 A | 11/1997 | |
| JP | 2002-012557 A | 1/2002 | |
| JP | 2003-055197 A | 2/2003 | |
| JP | 2003-525223 A | 8/2003 | |
| JP | 2007-525413 A | 9/2007 | |
| JP | 2008-508255 A | 3/2008 | |
| JP | 2008-517979 A | 5/2008 | |
| JP | 2008-526827 A | 7/2008 | |
| JP | 2015-533162 A | 11/2015 | |
| JP | 2017-532331 A | 11/2017 | |
| TW | 512167 B | 12/2002 | |
| WO | 92/22369 A1 | 12/1992 | |
| WO | 01/54683 A1 | 8/2001 | |
| WO | 02/47607 A2 | 6/2002 | |
| WO | 2004/066925 A2 | 8/2004 | |
| WO | 2006/045830 A1 | 5/2006 | |
| WO | 2006/072832 A1 | 7/2006 | |
| WO | 2008/036299 A2 | 3/2008 | |
| WO | 2009/108775 A2 | 9/2009 | |
| WO | 2011/063531 A1 | 6/2011 | |
| WO | 2013/024373 A1 | 2/2013 | |
| WO | 2013/183062 A2 | 12/2013 | |
| WO | WO-2014062444 A1 * | 4/2014 | ........... A61K 9/5042 |
| WO | 2017/080566 A1 | 5/2017 | |
| WO | 2020/169989 A1 | 8/2020 | |

OTHER PUBLICATIONS

Andrews. (2018) "How to Extract Oil from the Skin of Oranges," downloaded from https://www.weekand.com/ healthy-living/article/extract-oil-skin-oranges-18009337.php retrieved on Jun. 14, 2023; 4 pages.
Anonymous. (2013). "Making Orange Tincture," downloaded from https://boozyblog.wordpress.com/ 2013/08/05/making-orange-tincture/ retrieved on Jun. 14, 2023; 7 pages.
Anonymous. (2014). "Safety Data Sheet Orange Tincture," located at URL https://jmloveridge.com/wp-content/uploads/2018/06/Orange-Tincture-Version-06.pdf retrieved on Mar. 24, 2022; 6 pages.
Bourgou et al. (2012). "Changes of Peel Essential Oil Composition of Four Tunisian Citrus during Fruit Maturation," The Scientific World Journal; Article ID 528593; 10 pages.
Combined Search and Examination Report dated Apr. 28, 2020, directed to GB Application No. 2002466.7; 5 pages.
Combined Search and Examination Report dated Apr. 28, 2020, directed to GB Application No. 2002475.8; 7 pages.
Combined Search and Examination Report dated Apr. 28, 2020, directed to GB Application No. 2002479.0; 8 pages.
Combined Search and Examination Report dated Apr. 28, 2020, directed to GB Application No. 2002484.0; 7 pages.
Combined Search and Examination Report dated Nov. 22, 2021, directed to GB Application No. 2107172.5; 4 pages.
Combined Search and Examination Report dated Nov. 22, 2021, directed to GB Application No. 2107174.1; 4 pages.
Combined Search and Examination Report dated Nov. 22, 2021, directed to GB Application No. 2107177.4; 5 pages.
Deterre et al. (2014). "Classification of commercial bitter orange essential oils (*Citrus aurantium* L.), based on a combination of

(56) References Cited

OTHER PUBLICATIONS chemical and sensory analyses of specific odor markers," Journal of Essential Oil Research 26 (4), pp. 254-262.
Evonik-Glenn Corp. "Aerosil® R972," located at https://glenncorp.com/shop/aerosil-r-972/, retrieved on May 16, 2023.(1 page).
Examination Report dated Feb. 14, 2023, directed to GB Application No. 2002475.8; 3 pages.
Examination Report dated Feb. 6, 2023, directed to GB Application No. 2002466.7; 4 pages.
Examination Report dated Feb. 8, 2023, directed to GB Application No. 2107172.5; 3 pages.
First Office Action dated Nov. 3, 2022, directed to CN Application No. 202080015446.5; 22 pages.
International Search Report and Written Opinion dated Nov. 5, 2021, directed to International Application No. PCT/IB2021/056976; 15 pages.
International Search Report and Written Opinion mailed Apr. 17, 2020, directed to International Application No. PCT/GB2020/050419; 15 pages.
International Search Report and Written Opinion mailed Apr. 20, 2020, directed to International Application No. PCT/GB2020/050420; 13 pages.
International Search Report and Written Opinion mailed Apr. 21, 2020, directed to International Application No. PCT/GB2020/050422; 14 pages.
International Search Report and Written Opinion mailed Apr. 21, 2020, directed to International Application No. PCT/GB2020/050423; 14 pages.
Jabri Karoui et al. (2013). "Characterization of Bioactive Compounds in Tunisian Bitter Orange (*Citrus aurantium* L.) Peel and Juice and Determination of Their Antioxidant Activities," BioMed Research International; Article ID: 345415; 12 pages.
McLaughlin et al., Office Action dated Apr. 12, 2021, directed to U.S. Appl. No. 16/797,927; 21 pages.
McLaughlin et al., Office Action dated Apr. 13, 2021, directed to U.S. Appl. No. 16/798,130; 29 pages.
McLaughlin et al., Office Action dated Dec. 7, 2020, directed to U.S. Appl. No. 17/008,318; 16 pages.
McLaughlin et al., Office Action dated Dec. 9, 2020, directed to U.S. Appl. No. 17/008,108; 22 pages.
McLaughlin et al., Office Action dated Feb. 10, 2021, directed to U.S. Appl. No. 16/797,934; 24 pages.
McLaughlin et al., Office Action dated May 12, 2021, directed to U.S. Appl. No. 16/797,934; 22 pages.
McLaughlin et al., U.S. Advisory Action dated Jun. 21, 2023, directed to U.S. Appl. No. 16/798,067; 5 pages.
McLaughlin et al., U.S. Office Action dated Aug. 23, 2022, directed to U.S. Appl. No. 16/798,067; 15 pages.
McLaughlin et al., U.S. Office Action dated Aug. 29, 2023, directed to U.S. Appl. No. 16/798,067; 16 pages.
McLaughlin et al., U.S. Office Action dated Dec. 22, 2022, directed to U.S. Appl. No. 16/798,067; 14 pages.
McLaughlin et al., U.S. Office Action dated Feb. 6, 2023, directed to U.S. Appl. No. 17/307,638; 17 pages.
McLaughlin et al., U.S. Office Action dated Jun. 16, 2023, directed to U.S. Appl. No. 17/529,827; 26 pages.
McLaughlin et al., U.S. Office Action dated Jun. 8, 2023, directed to U.S. Appl. No. 17/390,331; 11 pages.
McLaughlin et al., U.S. Office Action dated Mar. 30, 2022, directed to U.S. Appl. No. 16/798,067; 20 pages.
McLaughlin et al., U.S. Office Action dated May 15, 2023, directed to U.S. Appl. No. 17/387,803; 18 pages.
McLaughlin et al., U.S. Office Action dated Sep. 13, 2023, directed to U.S. Appl. No. 17/387,803; 10 pages.
McLaughlin et al., U.S. Office Action dated Sep. 13, 2023, directed to U.S. Appl. No. 17/529,827; 15 pages.
National Center for Biotechnology Information. (Apr. 28, 2006). "Compound Summary—Simethicone," located at https://pubchem.ncbi.nlm.nih.gov/compound/Simethicone (2 pages).

O'Connell (May 2005). "Sieve Use in the Pharmaceutical Industry," Pharmaceutical Technology Europe 17(5): 7 pages.
Office Action dated Aug. 9, 2023, directed to MX Application No. MX/a/2021/009844; 5 pages.
Office Action dated Feb. 22, 2023, directed to IN Application No. 202127042578; 5 pages.
Office Action dated Feb. 27, 2023, directed to EP Application No. 20708584.6; 5 pages.
Office Action dated Jul. 10, 2023, directed to RU Application No. 2021127592; 37 pages.
Office Action dated Jul. 11, 2023, directed to MX Application No. MX/a/2021/009845; 6 pages.
Office Action dated Jul. 12, 2023, directed to RU Application No. 2021127591; 25 pages.
Office Action dated Jul. 14, 2023, directed to RU Application No. 2021127588; 22 pages.
Office Action dated Jul. 18, 2023, directed to TW Application No. 109105762; 14 pages.
Office Action dated Jul. 26, 2023, directed to TW Application No. 109105759; 12 pages.
Office Action dated Jul. 28, 2023, directed to IN Application No. 202127042579; 8 pages.
Office Action dated Jun. 1, 2023, directed to GB Application No. 2107172.5; 1 page.
Office Action dated Jun. 23, 2023, directed to MX Application No. MX/a/2021/009679; 6 pages.
Office Action dated Jun. 27, 2023, directed to MX Application No. MX/a/2021/009681; 6 pages.
Office Action dated May 2, 2023, directed to IN Application No. 202127042581; 6 pages.
Office Action dated May 22, 2023, directed to CN Application No. 202080015446.5; 8 pages.
Office Action dated May 31, 2023, directed to GB Application No. 2002466.7; 1 page.
Office Action dated May 31, 2023, directed to GB Application No. 2002475.8; 2 pages.
Office Action dated May 31, 2023, directed to IN Application No. 202127042580; 6 pages.
Office Action dated Sep. 13, 2023, directed to MX Application No. MX/a/2021/009679; 10 pages.
Syloid FG Silica (2015) "Syloid 244 FP silica: Formulation of viscous Simethicone in to chewable tablets," located at https://www.pharmaexcipients.com/wp-content/uploads/attachments/AP010_Syloid+244+FP-Formulation+of+Simethicone+into+chewable+tablets_Final.pdf?t=1458129627. (2 pages).
Written Opinion dated Nov. 2, 2022, directed to SG Application No. 11202108659X; 8 pages.
Written Opinion dated Nov. 2, 2022, directed to SG Application No. 11202109022U; 8 pages.
Written Opinion dated Nov. 2, 2022, directed to SG Application No. 11202109104X; 7 pages.
Written Opinion dated Nov. 3, 2022, directed to SG Application No. 11202108690Y; 11 pages.
Zhou et al. (Aug. 2013). "Improving manufacturability of an ibuprofen powder blend by surface coating with silica nanoparticles," Powder Technology 249: 290-296.
Office Action dated Apr. 18, 2024, directed to IL Application No. 285653; 4 pages.
Office Action dated Apr. 22, 2024, directed to MX Application No. MX/a/2021/009845; 5 pages.
Office Action dated Jun. 18, 2024, directed to MX Application No. MX/a/2021/009681; 11 pages.
Office Action dated May 7, 2024, directed to CN Application No. 202180051278.X; 20 pages.
Office Action dated May 6, 2024, directed to TW Application No. 109105773; 9 pages.
Office Action dated May 9, 2024, directed to MX Application No. MX/a/2021/009679; 10 pages.
McLaughlin et al., U.S. Office Action dated Mar. 7, 2024, directed to U.S. Appl. No. 16/798,067; 21 pages.
McLaughlin et al., U.S. Office Action dated Mar. 4, 2024, directed to U.S. Appl. No. 17/529,827; 19 pages.

(56) References Cited

OTHER PUBLICATIONS

Office Action dated Feb. 22, 2024, directed to MX Application No. MX/a/2021/009681; 8 pages.
Office Action dated Mar. 11, 2024, directed to JP Application No. 2021-549374; 11 pages.
Office Action dated Mar. 21, 2024, directed to IL Application No. 285640; 4 pages.
Office Action dated Mar. 27, 2024, directed to IL Application No. 285648; 4 pages.
Office Action dated Mar. 4, 2024, directed to IN Application No. 202127042580; 3 pages.
Office Action dated Mar. 5, 2024, directed to MX Application No. MX/a/2021/009844; 7 pages.
Huang et al., (2017). "Improving blend content uniformity via dry particle coating of micronized drug powders," European Journal of Pharmaceutical Sciences 104: 344-355.
McLaughlin et al., U.S. Office Action dated Jul. 17, 2024, directed to U.S. Appl. No. 16/798,067; 21 pages.
McLaughlin et al., U.S. Office Action dated Jul. 25, 2024, directed to U.S. Appl. No. 17/529,827; 23 pages.
McLaughlin et al., U.S. Office Action dated Dec. 7, 2023, directed to U.S. Appl. No. 17/390,331; 6 pages.
Office Action dated Dec. 11, 2023, directed to RU Application No. 2021127590; 24 pages.
Office Action dated Dec. 6, 2023, directed to RU Application No. 2021127592; 17 pages.
Office Action dated Dec. 7, 2023, directed to RU Application No. 2021127591; 14 pages.
Office Action dated Nov. 17, 2023, directed to MX Application No. MX/a/2021/009844; 6 pages.
Office Action dated Nov. 3, 2023, directed to TW Application No. 109105770; 8 pages.
Office Action dated Oct. 12, 2023, directed to MX Application No. MA/a/2021/009681; 9 pages.
Office Action dated Sep. 28, 2023, directed to PH Application No. 1/2021/552022; 4 pages.
Third Office Action dated Sep. 18, 2023, directed to CN Application No. 202080015446.5; 10 pages.
Bikiaris et al., (2007). "New Aspects in Sustained Drug Release Formulations," Recent Patents on Drug Delivery & Formulation 1(3): 201-213.
Extended European Search Report dated Jan. 23, 2024, directed to EP Application No. 23186234.3; 10 pages.
Extended European Search Report dated Jan. 31, 2024, directed to EP Application No. 23189317.3; 16 pages.
Gad, 2005. "Limonene," Encyclopedia of Toxicology (Second Edition), pp. 720-725.
Office Action dated Dec. 7, 2023, directed to TW Application No. 109105759; 8 pages.
Office Action dated Jan. 30, 2024, directed to MX Application No. MX/a/2021/009679; 9 pages.
Office Action dated Jan. 9, 2024, directed to JP Application No. 2021-549372; 9 pages.
Office Action dated Jan. 9, 2024, directed to JP Application No. 2021-549373; 12 pages.
Subsequent Substantive Examination Report dated Jan. 12, 2024, directed to EP Application No. 1/2021/552022; 4 pages.
Extended European search report dated Dec. 18, 2023, directed to EP Application No. 23183926.7; 8 pages.
First Office Action dated Dec. 27, 2023, directed to CN Application No. 202080015572.0; 34 pages.
Notice of Reasons for Rejection dated Dec. 4, 2023, directed to JP Application No. 2021-549375; 11 pages.
Office Action dated Dec. 12, 2023, directed to RU Application No. 2021127588; 16 pages.
Office Action dated Nov. 1, 2023, directed MX Application No. MX/a/2021/009845; 11 pages.
Office Action dated Nov. 4, 2023, directed to CN Application No. 202080015635.2; 23 pages.
Office Action dated Nov. 7, 2023, directed to TW Application No. 109105773; 10 pages.
Office Action dated Nov. 8, 2023, directed to TW Application No. 109105762; 10 pages.
Office Action dated Nov. 9, 2023, directed to CN Application No. 202080015564.6; 28 pages.
Office Action dated Jul. 13, 2023, directed to RU Application No. 2021127590; 30 pages.
Chueshov et al. (2002). Industrial Drug Technology. vol. 2; pp. 352-355.
Pertsev et al. (1999). Pharmaceutical and biomedical aspects of drugs, vol. 1; pp. 253-254.
Decision of Rejection dated Jul. 8, 2024, directed to JP Application No. 2021-549375; 7 pages.
Office Action dated Aug. 27, 2024, directed to BR Application No. 112021016405-7; 5 pages.
Office Action dated Aug. 30, 2024, directed to CN Application No. 202080015564.6; 28 pages.
Office Action dated Jul. 26, 2024, directed to CN Application No. 202080015635.2; 14 pages.
Office Action dated Oct. 1, 2024, directed to AU Application No. 2020223894; 3 pages.
Office Action dated Aug. 13, 2024, directed to JP Application No. 2021-549374; 5 pages.
Office Action dated Sep. 24, 2024, directed to AU Application No. 2020225818; 3 pages.
Office Action dated Sep. 26, 2024, directed to AU Application No. 2020225448; 4 pages.
Second Office Action dated Aug. 29, 2024, directed to CN Application No. 202080015572.0; 39 pages.
Blynskaya E.V. et al. (2019). "Features of the design of freeze-dried orallydisintegrating tablets," Pharmacy 68 (2): 17-23.
Cifuentes et al. (2013). "Critical points in ethylcellulose matrices: Influence of the polymer, drug and filler properties," Acta Pharm. 63: 115-129.
Decision on Rejection dated Nov. 13, 2024, directed to CN Application No. 202080015564.6; 29 pages.
Decision on Rejection dated Nov. 25, 2024, directed to CN Application No. 202080015572.0; 25 pages.
Murashkina et al. (2018). "Excipients in Pharmaceutical Technology," Study Guide, Irkutsk, Irkutsk State Medical University, pp. 6-9.
Office Action dated Dec. 10, 2025, directed to BR Application No. 112021016485-5; 5 pages.
Office Action dated Dec. 13, 2024, directed to RU Application No. 2023104317; 22 pages.
Office Action dated Nov. 28, 2024, directed to MX Application No. MX/a/2024/000693; 7 pages.
Sznitowska et al. (2005). "The Physical Characteristics of Lyophilized Tablets Containing a Model Drug in Different Chemical Formsand Concentrations," Acta Poloniae Pharmaceutica—Drug Research 62(1): 25-29.
Teckoe. (2017). "Coating compliance—looking at the important considerations when coating tablets," found online at https://www.sciencedirect.com/science/article/pii/S1090023302002691?via=ihub; 6 pages.
Yilmaz et al. (2003). "Evaluation of virucidal activity of three commercial disinfectants and formic acid using bovine enterovirus type 1 (ECBO virus), mammalian orthoreovirus type 1 and bovine adenovirus type 1," The Veterinary Journal 166: 67-78.
Communication pursuant to Article 94(3) EPC dated Feb. 3, 2025, directed to EP Application No. 21752210.1; 9 pages.
Office Action dated Mar. 4, 2025, directed to EP Application No. 23183926.7; 7 pages.
Substantive Examination Report dated Jan. 15, 2025, directed to PH Application No. 1-2021-552026; 4 pages.
Substantive Examination Report dated Nov. 15, 2024, directed to PH Application No. 1-2021-552019; 5 pages.

* cited by examiner

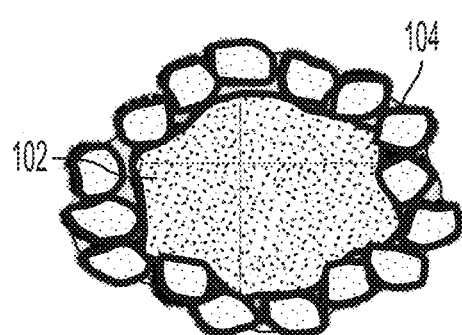
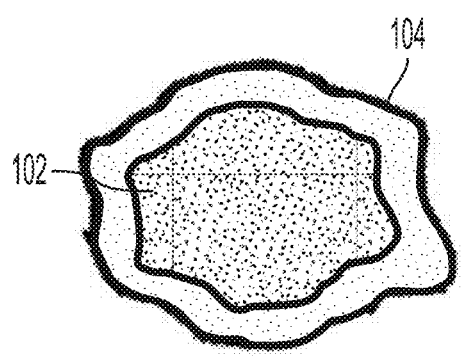
FIG. 1A
FIG. 1B
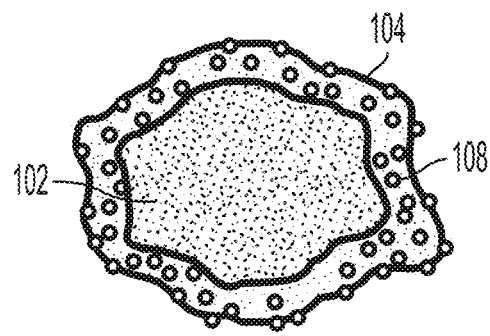
FIG. 1C
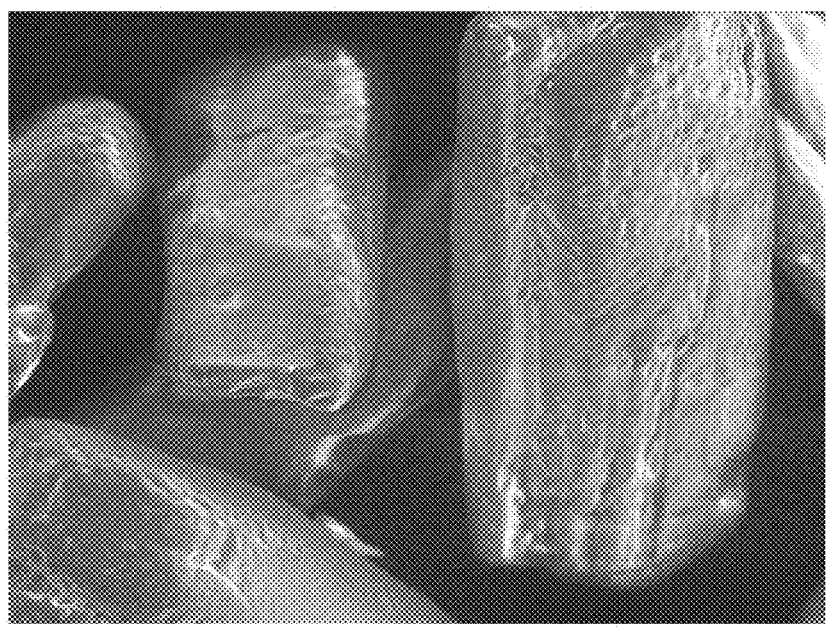
FIG. 2

MINIMIZING AGGLOMERATION OF DRUG PARTICLE COATING MATERIAL DURING STORAGE TO STABILIZE DISINTEGRATION TIMES OF PHARMACEUTICAL PRODUCTS

CROSS REFERENCE TO RELATED APPLICATIONS

This application is a continuation of U.S. application Ser. No. 17/307,638, filed May 4, 2021, which is a divisional of U.S. application Ser. No. 17/008,318, filed Aug. 31, 2020, which is a continuation of U.S. application Ser. No. 16/797,927, filed Feb. 21, 2020, which claims the priority of U.S. Provisional Application No. 62/809,307, filed Feb. 22, 2019, the entire contents of each of which are incorporated herein by reference.

FIELD

This relates to processes for coating active pharmaceutical ingredient (API) particles, and more particularly, to processes that minimize excess coating material to prevent agglomeration of the coated material in a lyophilized orally disintegrating dosage form during storage.

BACKGROUND

Pharmaceutical compositions typically include both an active pharmaceutical ingredient as well as one or more inactive ingredients. The active pharmaceutical ingredient (API) is biologically active and is designed to directly affect a patient's symptoms, diseases, disorders, and/or ailments. The inactive ingredient(s) of a pharmaceutical composition, on the other hand, are pharmaceutically inert and can be used for various purposes including, but not limited to, improving long-term stabilization, filling or diluting a solid formulation, facilitating drug absorption, modifying viscosity of liquid formulations, enhancing solubility and/or aiding the manufacture of the pharmaceutical composition.

In addition, some inactive ingredients may be used to mask the taste of the API. Many APIs are known to exhibit unpleasant organoleptic properties if allowed to dissolve in the oral cavity, such as bitter taste, burning sensation and numbing. For example, some orally-administered pharmaceutical compositions are designed to disperse in the mouth to enable administration without water and are targeted to pediatric patients, geriatric patients, animal patients, and/or other types of patients that may have difficulties swallowing. For these types of orally-administered pharmaceutical compositions, an inactive ingredient may be used to form a "functional coating" to mask the taste of the API.

For example, an inactive ingredient may be used to mask the taste of the API by wet coating or dry coating the API particle to produce a functional coating surrounding the API particles such that it prevents API release in the mouth. In wet particle coating, inactive ingredients (polymer and additives) are dissolved or dispersed in solvent or water to form a suspension or solution. This suspension or solution can then be sprayed onto the surface of the API particles to form a coating of film by evaporation of the solvent or water. Examples of technologies for wet particle coating include microencapsulation, fluid bed coating, spray drying, pan coating etc. In dry particle coating (also referred to as solventless coating), API particles are physically coated with fine particles of inactive ingredients (polymer and additives) to form particle composites. Examples of dry particle coating include hot melt coating, supercritical coating, impaction coating, electrostatic coating. API particles coated with a taste-masking inactive ingredient may provide a more pleasant experience for a patient having difficulties swallowing or having a sensitivity to taste that would otherwise lead to a negative patient experience and poor compliance.

For example, a dry, solventless mixing method may use high energy vibrations or acoustic resonance to mix the API with the inactive ingredient(s). Further, coating an API particle with a functional coating may temporarily delay the release of the API in a patient's mouth during dispersion of the pharmaceutical composition, yet still allow at least 90% of the API that would be released without the coating to be released from the functionally-coated API within a suitable amount of time for absorption. Coating the API in a taste-masking inactive ingredient allows the dissolution rate of the coated API particle to be controlled such that a majority of the API is not released until after the coated API particle has passed to a patient's stomach.

SUMMARY

Provided are methods for minimizing agglomeration of coating material for coated API particles produced using various mixing processes. API particles that are coated using conventional mixing processes often experience agglomeration of excess coating material, particularly upon storage. Agglomeration of coating material can decrease the stability of the pharmaceutical product over time. For example, a pharmaceutical product's disintegration time may increase over time if it comprises agglomerated coating material. An increased disintegration times and/or a decreased dissolution rate implies an unstable pharmaceutical product. An unstable pharmaceutical product can lead to a shorter shelf life than desired. Accordingly, embodiments provided may help minimize agglomeration of coating material for coated API particles to improve the stability of the pharmaceutical product during storage and to increase its shelf life.

For example, methods described include removing excess coating material from the coated API particles to minimize the possibility of agglomeration of the coating material particles. Particularly, methods provided include sieving the coated API particles such that the final pharmaceutical product is adequately surrounded by dry matrix, minimizing any agglomeration of coating material particles upon storage. Pharmaceutical compositions described provide for a disintegration time and a dissolution rate that remain relatively stable over time.

In some embodiments, a pharmaceutical composition is provided, the pharmaceutical composition comprising: 65-85% w/w API particles; 15-30% w/w coating material coating the API particles; and 3-15% w/w matrix surrounding the coated API particles, wherein the pharmaceutical composition comprises a disintegration time of less than 10 seconds for at least six months under storage conditions of at least 25° C. and at least 60% relative humidity. In some embodiments, the coating material comprises a first coating material and a second coating material and the pharmaceutical composition comprises 10-30% w/w the first coating material and 0.5-10% w/w the second coating material. In some embodiments, the first coating material comprises wax. In some embodiments, the second coating material comprises silica. In some embodiments of the pharmaceutical composition, the pharmaceutical composition comprises a disintegration time of less than 10 seconds for at least six months under storage conditions of at least 30° C. and at least 65% relative humidity. In some embodiments of the pharmaceutical composition, the pharmaceutical composition comprises a disintegration time of less than 10 seconds for at least six months under storage conditions of at least 40° C. and at least 75% relative humidity. In some embodiments of the pharmaceutical composition, the API particles comprise one or more of anti-inflammatories, analgesics, anti-psychotics, anti-emetics, laxatives, anti-diarrheals, anti-histamines, or anti-depressants. In some embodiments of the pharmaceutical composition, the coating material comprises silica as one or more of a protectant or a flow aid. In some embodiments of the pharmaceutical composition, wherein the coating material comprises a wax. In some embodiments of the pharmaceutical composition, the coating material comprises one or more of carnauba wax, candelilla wax, or synthetic wax. In some embodiments of the pharmaceutical composition, a coating ratio used to combine the API particles with the coating material comprises 5-85% w/w coating material and 15-95% w/w uncoated API particles. In some embodiments of the pharmaceutical composition, the matrix comprises a matrix former and a structure former. In some embodiments of the pharmaceutical composition, the matrix former comprises one or more of a water soluble material, a water dispersible material, a polypeptide, a polysaccharide, polyvinyl alcohol, polyvinylpyrrolidone, and acacia. In some embodiments of the pharmaceutical composition, the matrix former comprises a polypeptide. In some embodiments of the pharmaceutical composition, the polypeptide comprises gelatin. In some embodiments of the pharmaceutical composition, the structure former comprises one or more of mannitol, dextrose, lactose, galactose, and cyclodextrin. In some embodiments of the pharmaceutical composition, the structure former comprises mannitol.

In some embodiments, a pharmaceutical composition is provided, the pharmaceutical composition prepared by a process comprising the steps of: coating API particles with a first coating material to form coated API particles, wherein the coating material comprises one or more deformable components; applying mechanical stress to the coated API particles to deform the one or more deformable components; coating the coated API particles with silica; applying mechanical stress to embed the silica into the coated API particles; sieving the coated API particles to remove excess coating materials, wherein the excess coating materials comprise coating materials not bound to a coated API particle; mixing the coated API particles into a matrix solution/suspension to form a pharmaceutical suspension; and dosing the pharmaceutical suspension into a mold, wherein the pharmaceutical composition comprises a disintegration time of less than 10 seconds for at least six months under storage conditions of at least 25° C. and at least 60% relative humidity. In some embodiments of the pharmaceutical composition, a dosing ratio used to combine the coated API particles with the matrix solution/suspension comprises 5-60% w/w coated API particles to 40-95% w/w matrix solution/suspension. In some embodiments of the pharmaceutical composition, a coating ratio used to combine the API particles with the coating material comprises 5-85% w/w coating material and 15-95% w/w uncoated API particles. In some embodiments of the pharmaceutical composition, the pharmaceutical composition comprises freezing the dosed suspension under sub-zero conditions and freeze-drying to form a lyophilized pharmaceutical composition. In some embodiments of the pharmaceutical composition, the pharmaceutical composition comprises a disintegration time of less than 10 seconds for at least six months under storage conditions of at least 30° C. and at least 65% relative humidity. In some embodiments of the pharmaceutical composition, the pharmaceutical composition comprises a disintegration time of less than 10 seconds for at least six months under storage conditions of at least 40° C. and at least 75% relative humidity. In some embodiments of the pharmaceutical composition, the pharmaceutical composition comprises 65-85% w/w API particles. In some embodiments of the pharmaceutical composition, the pharmaceutical composition comprises 15-30% w/w coating material. In some embodiments of the pharmaceutical composition, the pharmaceutical composition comprises 3-% w/w matrix. In some embodiments of the pharmaceutical composition, the method used to prepare the pharmaceutical composition comprises sieving uncoated API particles. In some embodiments of the pharmaceutical composition, sieving the coated API particles comprises passing the coated API particles through a device comprising two or more sieves. In some embodiments of the pharmaceutical composition, sieving the coated API particles comprises sieving the coated API particles to an average particle size of 75 μm or greater. In some embodiments of the pharmaceutical composition, sieving the coated API particles comprises sieving the coated API particles to an average particle size of 200 μm or less. In some embodiments of the pharmaceutical composition, the API particles comprise one or more of anti-inflammatories, analgesics, anti-psychotics, anti-emetics, laxatives, anti-diarrheals, anti-histamines, or anti-depressants. In some embodiments of the pharmaceutical composition, the coating material comprises silica as one or more of a protective coat or a flow aid. In some embodiments of the pharmaceutical composition, the one or more deformable components of the coating material comprises a wax. In some embodiments of the pharmaceutical composition, the wax comprises one or more of carnauba wax, candelilla wax, or synthetic wax. In some embodiments of the pharmaceutical composition, the matrix comprises a matrix former and a structure former. In some embodiments of the pharmaceutical composition, the matrix former comprises one or more of a water soluble material, a water dispersible material, a polypeptide, a polysaccharide, polyvinyl alcohol, polyvinylpyrrolidone, and acacia. In some embodiments of the pharmaceutical composition, the matrix former comprises a polypeptide. In some embodiments of the pharmaceutical composition, the polypeptide comprises gelatin. In some embodiments of the pharmaceutical composition, the structure former comprises one or more of mannitol, dextrose, lactose, galactose, and cyclodextrin. In some embodiments of the pharmaceutical composition, the structure former comprises mannitol.

In some embodiments, a method of treating a patient is provided, the method comprising administering to a patient a therapeutic amount of the pharmaceutical composition. In some embodiments of the method, the patient is a human.

In some embodiments, a method of preparing a pharmaceutical composition is provided, the method comprising: coating API particles with a first coating material to form coated API particles, wherein the coating material comprises one or more deformable components; applying mechanical stress to the coated API particles to deform the one or more deformable components of the coating material to form a continuous film layer over the surface of the API particles; coating the coated API particles with silica to form a second coat by applying mechanical stress to partially embed or embed the silica into the deformable coat; sieving the coated API particles to remove excess coating materials; mixing the coated API particles into a matrix solution/suspension to form a pharmaceutical suspension; and dosing the pharmaceutical suspension into a mold. In some embodiments of the method, a dosing ratio used to combine the coated API particles with the matrix solution/suspension comprises 5-60% w/w coated API particles to 40-95% w/w matrix solution/suspension. In some embodiments of the method, a coating ratio used to combine the API particles with the coating material comprises 5-85% w/w coating material and 15-95% w/w uncoated API particles. In some embodiments of the method, the method comprises freezing the dosed suspension under sub-zero temperatures and freeze-drying to form a lyophilized pharmaceutical composition. In some embodiments of the method, the method comprises sieving uncoated API particles. In some embodiments of the method, sieving the coated API particles comprises passing the coated API particles through a device comprising two or more sieves. In some embodiments of the method, sieving the coated API particles comprises sieving the coated API particles to an average particle size of 75 µm or greater. In some embodiments of the method, sieving the coated API particles comprises sieving the coated API particles to an average particle size of 200 µm or less. In some embodiments of the method, the API particles comprise one or more of anti-inflammatories, analgesics, anti-psychotics, anti-emetics, laxatives, anti-diarrheals, anti-histamines, or anti-depressants. In some embodiments of the method, the coating material comprises silica as one or more of a protective coating or a flow aid. In some embodiments of the method, the one or more deformable components of the coating material comprises a wax.

In some embodiments of the method, the wax comprises one or more of carnauba, candelilla wax, or synthetic wax. In some embodiments of the method, the matrix comprises a matrix former and a structure former. In some embodiments of the method, the matrix former comprises one or more of a water soluble material, a water dispersible material, a polypeptide, a polysaccharide, polyvinyl alcohol, polyvinylpyrrolidone, and acacia. In some embodiments of the method, the matrix former comprises a polypeptide. In some embodiments of the method, the polypeptide comprises gelatin. In some embodiments of the method, the structure former comprises one or more of mannitol, dextrose, lactose, galactose, and cyclodextrin. In some embodiments of the method, the structure former comprises mannitol.

BRIEF DESCRIPTION OF THE DRAWINGS

The invention will now be described, by way of example only, with reference to the accompanying drawings, in which:

FIG. 1A shows an API particle coated with particles of a deformable coating material (i.e., a first coating layer) according to some embodiments;

FIG. 1B shows an API particle coated with a continuous film layer of deformable coating material (i.e., a first coating layer) according to some embodiments;

FIG. 1C shows an API particle coated with a continuous film layer of deformable coating material (i.e., a first coating layer) with particles of silica (i.e., a second coating layer) partially embedded and/or embedded on the surface of the first coating layer according to some embodiments;

FIG. 2 shows a scanning electron microscope (SEM) image of an un-coated API particle according to some embodiments;

DETAILED DESCRIPTION

Figure 3:
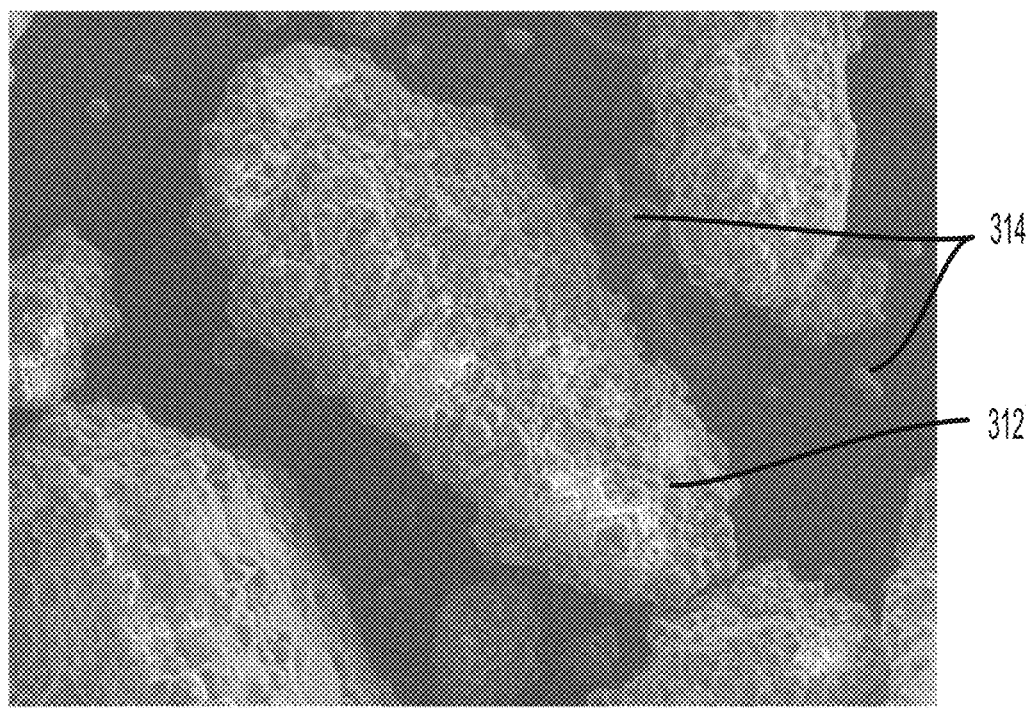
FIG. 3 shows an SEM image of a coated API particle according to some embodiments.

Described herein are exemplary embodiments of methods for minimizing and/or preventing the agglomeration of the coating material of coated API particles. Particularly, methods according to some embodiments include removing excess coating material particles to minimize and/or to prevent agglomeration of coating material in a pharmaceutical product. In some embodiments, methods may include sieving the raw API particles and/or the coated API particles. Specifically, methods provided may include sieving the API particles and/or the coated API particles to remove any undesired particles, such as excess coating material particles. Sieving processes according to embodiments disclosed may help prevent and/or minimize the potential of coating material agglomeration that can adversely affect a disintegration time and/or a dissolution rate of the final product.

Methods for minimizing and or preventing agglomeration of coating material particles according to embodiments described herein may be applied to dry, solventless mixing processes for coating API particles. Accordingly, methods provided are described below in context of one or more dry, solventless mixing processes for coating API particles. However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Generally, a solventless mixing process for coating API particles includes mixing coating materials with API particles to produce coated API particles. The coated API particles are then stressed mechanically and/or thermally to deform the deformable coating material, creating a continuous film surrounding the API particles. The coated API particles are then placed into a matrix solution/suspension to form a pharmaceutical suspension. The pharmaceutical suspension comprising the coated API particles can be dosed into preformed molds, such as blister packs, and further treated to produce a dispensable pharmaceutical composition (e.g., a lyophilizate, a wafer, a tablet, etc.).

However, when the final product is stored, any excess coating material particles not bound to a coated API particle can agglomerate. The amount and/or severity of agglomeration may increase over time. Agglomeration of excess coating material can increase the disintegration times and/or decrease the dissolution rate of the pharmaceutical product and adversely affect any functional properties of the coating material. An increased disintegration time may also cause unacceptable dispersion and mouthfeel characteristics in vivo.

Accordingly, it has been discovered that by sieving the coated API particles, excess coating material can be removed, thus minimizing the amount of agglomeration of excess coating material upon storage. Further, some embodiments include optimizing the coating ratio (amount of coating materials to the amount of uncoated API) and optimizing the dosing ratio (amount of coated API particles to the matrix solution/suspension comprising all the other inactive ingredients) can also minimize the agglomeration of excess coating material particles.

Embodiments provided herein can be applied to coated API particles produced using dry, solventless processes. For example, processes according to some embodiments may be designed particularly to produce pharmaceutical compositions comprising APIs with a poor taste that may be administered to pediatric patients, geriatric patients, animal patients, and/or other types of patients that may have difficulties swallowing or may be sensitive to taste. In particular, many APIs have an undesirable taste and/or a numbing effect that may be problematic for these patients. Accordingly, some mixing processes according to embodiments described herein include coating API particles with a taste-masking coating. Such coatings can control the disintegration time and/or the dissolution rate of an orodispersible pharmaceutical composition such that the release of the API upon oral administration is delayed or significantly reduced during the first few minutes when it is in the mouth, yet a satisfactory amount of the API is released within 30 minutes from oral administration post swallowing. (For example, a satisfactory amount of API may be 90% of the API amount which would be released without the coating). U.S. Pat. No. 9,107,851 (the '851 patent) is directed to an example dry, solventless process for coating pharmaceutical ingredients, the entirety of which is incorporated herein.

However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Additionally, specific data as provided herein is related to disintegration times. However, disintegration time is inversely related to dissolution rates. Thus, the data inherently provides information on dissolution rates as well. Disintegration time may be measured according to methods set forth by the United States Pharmacopeia (Disintegration 701). In some embodiments, the disintegration time may be from 2-30 seconds or 5-20 seconds. In some embodiments, the disintegration time may be less than 30 seconds, less than 25 seconds, less than 20 seconds, less than 15 seconds, less than 10 seconds, or less than 5 seconds. In some embodiments, the disintegration time may be greater than 2 seconds, greater than 5 seconds, greater than 10 seconds, greater than 15 seconds, greater than 20 seconds, or greater than 25 seconds. Similarly, dissolution rate may also be tested according to methods set forth by the United States Pharmacopeia (Dissolution 711).

FIGS. 1A, 1B, and 1C illustrate different phases of a coated API particle according to some embodiments. In some embodiments, API particles can be combined with one or more coating materials to produce coated API particles. This coating may comprise materials including a water soluble and/or water swellable material and a water insoluble material (described in detail below).

For example, FIG. 1A shows an API particle 102 surrounded by particles of a coating material 104. To achieve the coated API particle of FIG. 1A, the combined API particles (i.e., API particle 102) and one or more coating material(s) (i.e., coating material particles 104) may be exposed to mechanical and/or thermal energy to produce an ordered mixture of API particles 102 comprising a discrete layer of coating material particles 104 layering the surface of the API particle 102. API particle 102 of FIG. 1A is shown with a single layer of discrete particles of coating material(s). However, API particle 102 may have two or more discrete layers of coating particles. Additionally, FIG. 2 shows an SEM image of an un-coated API particle.

FIG. 1B demonstrates API particle 102 surrounded by continuous, deformed film layer 104. Specifically, FIG. 1B shows that all of the coating material particles 104 may be deformable and may deform when subjected to mechanical stress and/or elevated temperature. Thus, because all the coating materials comprise deformable characteristics, the coating material 104 of FIG. 1B is a relatively smooth and continuous coating layer after exposure to mechanical and/or thermal energy. In some embodiments, API particle 102 may have two or more relatively smooth and continuous coating layers. "Continuous film" as used herein may be a layer surrounding an API particle formed by melting/softening or otherwise breaking down one or more deformable components of the individual coating material particles such that they comprise a single, continuous layer surrounding the API particle. FIG. 3 also provides an SEM image showing a coated API particle according to some embodiments.

In some embodiments, one or more of the coating materials may not be deformable but may be embedded in the deformable coating layer. Thus, the continuous film may comprise solid particles of the non-deformable material embedded within the deformed coating material. FIG. 1C shows that continuous film 104 may comprise solid non-deformable particles 108 of one or more non-deformable materials partially embedded and/or embedded within the deformed coating material of continuous film 104. This continuous film 104 of FIG. 1B or 1C can ensure a coating (for example, a coating that masks the taste of the API) and a delayed API release. In some embodiments, API particle 102 may have two or more continuous coating layers partially embedded and/or embedded with non-deformable coating material particles. FIG. 3 also provides an SEM image showing a functionally-coated API particle according to some embodiments.

As used herein, the terms "deformable", "deformable components", "deformable components of the coating material" and other related terms refer to one or more components of the water soluble, water swellable, and/or water insoluble materials that can be broken down when subjected to mechanical stress and/or elevated temperature.

API particle 102 of the coated API particles may be any of numerous APIs. FIG. 2 shows an SEM image of an un-coated API particle according to some embodiments. As used herein, "active pharmaceutical ingredient" or "API" refers to a drug product that may be used in the diagnosis, cure, mitigation, treatment, or prevention of disease. Any API may be used for purposes of the present disclosure. Suitable APIs include, without limitation: analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, antihypertensive agents, anti-malarials, anti-migraine agents, anti-muscarinic agents, anti-neoplastic agents and immunosuppressants, anti-protazoal agents, anti-psychotics, anti-emetics, anti-rheumatics, anti-thyroid agents, antivirals, anxiolytics, aperients, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, laxatives, lipid regulating agents, local anesthetics, neuromuscular agents, nitrates and anti-anginal agents, nutritional agents, opioid analgesics, oral vaccines, proteins, peptides and recombinant drugs, purgatives, sex hormones and contraceptives, spermicides, and stimulants; and combinations thereof. A list of specific examples of these API may be found in U.S. Pat. No. 6,709,669, which is incorporated herein by reference. When present, the API is present in the pharmaceutical formulation in an amount that is necessary to exhibit the required physiological effect as established by clinical studies. One of ordinary skill in the art can readily determine an appropriate amount of API to include in the dosage form made according to the present disclosure.

In some embodiments, the coated API particles or pharmaceutical compositions may comprise from 30.0 to 90.0% w/w API. In some embodiments, the coated API particles or pharmaceutical compositions may comprise from 40.0 to 85.0% w/w, from 50.0 to 80.0% w/w, or from 70.0 to 80.0% w/w API. In some embodiments, the coated API particles or pharmaceutical compositions may comprise more than 40.0% w/w, more than 50.0% w/w, more than 60.0% w/w, more than 65% w/w, more than 70.0% w/w, more than 75.0% w/w, more than 80.0% w/w, or more than 85.0% w/w API. In some embodiments, the coated API particles or pharmaceutical compositions may comprise less than 90.0% w/w, less than 85.0% w/w, less than 80.0% w/w, less than 75.0% w/w, less than 70.0% w/w, less than 60.0% w/w, less than 50.0% w/w, or less than 40.0% w/w API.

In some embodiments, raw API particles may be sieved prior to the coating process to achieve a narrower particle size range. For example, the raw API particles may be sieved to remove oversized particles and/or to remove undersized particles. In some embodiments, more than one mesh can be used to remove certain particles. For example, a sieving device may comprise a series of two or more meshes to remove particles of a certain size according to the size of the mesh(s). The sieve can incorporate a vacuum transfer system to transport the particles through the series of meshes of the device. Additionally, ultrasonic probes may be incorporated into the sieving device to improve material flow and minimize blinding of the mesh during processing.

In some embodiments, the raw API particles can be sieved using a mesh size from 30 μm to 500 μm, from 50 μm to 450 μm, from 100 μm to 400 μm, from 150 μm to 350 μm, or from 200 μm to 300 μm. In some embodiments, the raw API particles can be sieved using a mesh size less than 500 μm, less than 450 μm, less than 400 μm, less than 350 μm, less than 300 μm, less than 250 μm, less than 200 μm, less than 150, or less than 100 μm. In some embodiments, the raw API particles can be sieved using a mesh size greater than 30 μm, greater than 50 μm, greater than 100 μm, greater than 150 μm, greater than 200 μm, greater than 250 μm, greater than 300 μm, greater than 350 μm, or greater than 400 μm.

Coating 104 surrounding the API particle 102 may comprise materials including a water soluble and/or water swellable material and a water insoluble material. In some embodiments, this coating may coat an API particle directly, or it may coat an API particle already comprising one or more coatings. In some embodiments, the ratio of coating material to API particles may be optimized to minimize excess coating material. For example, the coating material may comprise 5-85% w/w, 10-50%, 15-30% of the API and coating material mixture or final pharmaceutical composition. In some embodiments, the coating material may comprise less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the API and coating material mixture or final pharmaceutical composition. In some embodiments, the coating material may include more than 5%, more than 10%, more than 15%, more than 20%, more than 25%, more than 30%, more than 35%, more than 40%, more than 45%, more than 50%, more than 55%, more than 60%, more than 65%, more than 70%, or more than 75% of the API and coating material mixture or final pharmaceutical composition. In some embodiments, the coating material percentage may include two or more layers of coating material.

The water swellable material of the coating material may be a particle comprising a median particle size of about 0.5 μm to about 20 μm or about 1 μm to about 10 μm. In some embodiments, the water swellable material may be approximately ten times smaller than that of the API to enable ordered mixing and coating. The water swellable material can swell upon absorption of water such that a diameter of the water swellable particle increases at least by about 120-600%. The coating material or pharmaceutical composition may comprise from 0 to 8% w/w or from 0.1 to 0.9% w/w water swellable materials. In some embodiments, the coating material or pharmaceutical composition may comprise from 0.5 to 6.0% w/w, from 1.0 to 4.0% w/w, from 1.5 to 3.5% w/w, or from 2.0 to 3.0% w/w water swellable materials. In some embodiments, the coating material or pharmaceutical composition may comprise less than 8.0% w/w, less than 6.0% w/w, less than 4.0% w/w, less than 2.0% w/w, less than 1.0% w/w, or less than 0.5% w/w water swellable materials. In some embodiments, the coating material or pharmaceutical composition may comprise greater than 0.1% w/w, greater than 0.5% w/w, greater than 1.0% w/w, greater than 2.0% w/w, greater than 3.0 w/w %, greater than 5.0% w/w, or greater than 6.0% w/w water swellable materials. The water swellable material of the coating material may be deformable under mechanical stress and/or elevated temperature (described in detail below). The water swellable material may be any one or more of crospovidone, croscarmellose, sodium starch glycolate, or any other suitable disintegrant used in the pharmaceutical industry as an additive or blend made for tableting.

The water soluble material of the coating material may also be a particle comprising a median particle size of about 0.5 μm to about 20 μm or about 1 μm to about 10 μm. In some embodiments, the water soluble material may be approximately ten times smaller than that of the API to enable ordered mixing and coating. The water soluble material may have a water solubility of at least about 50 mg/ml in water at a neutral pH and at 20° C. Further, the water soluble material can have an intrinsic dissolution rate of about 3-60 μg/m$^2$s. The water soluble material of the coating material may be deformable under mechanical energy and/or thermal energy. The coating material or pharmaceutical composition may comprise from 0 to 35% w/w water soluble materials. In some embodiments, the coating material or pharmaceutical composition may comprise from 0.5 to 25% w/w, from 1.0 to 15% w/w, from 1.5 to 10% w/w, or from 2.0 to 3.0% w/w water soluble materials. In some embodiments, the coating material or pharmaceutical composition may comprise less than 35% w/w, less than 30% w/w, less than 25% w/w, less than 20% w/w, less than 15% w/w, less than 10% w/w, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, or less than 0.5% w/w water soluble materials. In some embodiments, the coating material or pharmaceutical composition may comprise more than 0.1% w/w, more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 8.0% w/w, more than 10% w/w, more than % w/w, more than 20% w/w, more than 25% w/w, or more than 30% w/w water soluble materials. The water soluble material may be one or more of sucrose, mannitol, sorbitol, polyvinylpyrrolidone, hydroxypropylcellulose, lactose, poly-(ethylene oxide), and any other suitable micronizable materials or polyols.

In addition to an intrinsic dissolution rate of 3-60 μg/m$^2$s discussed above, processes provided can permit the use of water soluble and/or water swellable materials having a higher intrinsic dissolution rate of about 60-300 µg/m²s as well. However, API particles with coating materials having a higher intrinsic dissolution rate should be dry coated with hydrophobic silica. Dry coating API particles wherein the coating comprises water soluble and/or water swellable materials having higher intrinsic dissolution rates can increase the disintegration time of the API, such that they are incapable of masking the API's taste effectively. Accordingly, dry coating the API particles with silica as a second coating material to slow the dissolution rate can improve the in-vivo taste-masking performance of the coating. The coated API may comprise from 0.5 to 35% w/w silica. In some embodiments, the coated Ibuprofen or final pharmaceutical composition can comprise from 0.5 to 20% w/w, from 0.5 to 10% w/w, or from 0.5 to 5% w/w hydrophobic fumed silica. In some embodiments, the coated Ibuprofen or final pharmaceutical composition can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w hydrophobic fumed silica. In some embodiments, the coated Ibuprofen or final pharmaceutical composition can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, or less than 1.0% w/w hydrophobic fumed silica. Examples of silica that may be used include, but are not limited to, Aerosil R972 silica (Degussa), CAB-O-SIL EH-5 silica (Cabot), OX-50 silica (Degussa), COSM055 (Catalyst & Chemical Ind. Co. Ltd (Japan)), P-500 hydrophilic silica (Catalyst & Chemical Ind. Co. Ltd (Japan)), and TS5 silica (Cabot). Further, suitable devices that may be used to dry coat with silica include, but are not limited to, Comil (U3 Quadro Comil of Quadro Pennsylvania, U.S.), LabRAM (Resodyne Minnesota, U.S.), Magnetically Assisted Impact Coater (MAIC, Aveka Minnesota, U.S.), and Fluid Energy Mill (FEM, Qualification Micronizer of Sturtevant Massachusetts U.S.).

The water insoluble material of the coating materials may also be a particle comprising an average particle size less than that of the API. For example, the water insoluble material(s) may comprise an average particle size from about 1-20 µm, about 1-12 µm, about 2-10 µm, about 5-12 µm, or about 5-6 µm. In some embodiments, the water insoluble material may be approximately ten times smaller than that of the API to enable ordered mixing and coating. The water insoluble material of the coating material may be deformable under mechanical stress and/or elevated temperature. The coating material or pharmaceutical composition may comprise from 5 to 70% w/w, from 10 to 60% w/w, from 10 to 50% w/w, from 10 to 40% w/w, from 10 to 35% w/w, or from 15 to 30% w/w water insoluble materials. In some embodiments, the coating material or pharmaceutical composition may comprise more than 5% w/w, more than 10% w/w, more than 15% w/w, more than 20% w/w, more than 25% w/w, more than 30% w/w, more than 35% w/w, or more than 40% w/w water insoluble materials. In some embodiments, the coating material or pharmaceutical composition may comprise less than 70% w/w, less than 60% w/w, less than 50% w/w, less than 45% w/w, less than 40% w/w, less than 35% w/w, or less than 30% w/w water insoluble materials. Examples of suitable water insoluble materials include, but are not limited to ethylcellulose, polyethylene, polypropylene, polytetrafluoroethylene, carnauba wax, candelilla wax, castor wax, polyamide wax and/or synthetic wax.

In some embodiments, mechanical and/or thermal energy may be used to deform the one or more water insoluble materials, water swellable materials, and/or water insoluble materials. For example, mechanical stress can be applied to the functionally-coated API particles using a PharmaRAM II acoustic mixer, a RAM 5 Pharma mixer, or a RAM 55 Pharma mixer (Resodyn Mixers). The coated API particles may be exposed to up to 100 times the force of gravity (100G acceleration) during this acoustic mixing process. These high forces cause particle-particle collisions that generate energy in the form of heat, which may be used to deform the one or more water insoluble materials, water swellable materials, and/or water insoluble materials onto the API.

Mixing the deformable coating materials with the API particles in this step produces API particles surrounded or covered with coating material particles, as illustrated in FIG. 1A. FIG. 1A shows API particle 102 coated with individual coating material particles 104, to create a coated API particle. In some embodiments, the coated API can be further coated with a second non coating material, as illustrated in FIG. 1C. FIG. 1C shows API particle 102 coated with layer deformable coating material 104 and partially embedded and embedded with particles of second coating material 108.

However, the coating process described above can also generate "loose", or "free" coating material particles. FIG. 2 is an SEM image of an uncoated API particle. FIG. 3 is an SEM image of coated API particle 312. However, "loose" or "free" coating material particles 314 are not bound to coated API particle 312.

Once the API particles have been coated by the coating material to produce coated API particles, the coated API particles may be sieved to remove excess coating material and residual fine API particles, either uncoated, partially coated or coated. Excess coating material may include any coating material particles not bound to a coated API particle. Upon storage of the final pharmaceutical composition (i.e., product), any excess coating material can agglomerate. For example, fusion may occur between excess coating particles and coating particles that are already bound to an API particle, preventing ingress of media that would otherwise aid in disintegration of the unit or tablet or dissolution of the coated API particle. Accordingly, agglomeration of excess coating material can cause increased disintegration times and/or decreased dissolution rates upon administration.

However, it has been determined that methods of sieving excess coating material from the coated API particles can minimize agglomeration of the coating material and maintain the initial disintegration time and/or dissolution rate of the final product. The sieving process can be either batch or continuous. Additionally, this sieving process may be performed in addition to or in lieu of the sieving process performed on raw API particles, described above. In some embodiments, the sieving process parameters may be different between the uncoated, raw API particles and the coated API particles.

In some embodiments, coated API particles may be sieved to remove coating material particles having an average particle size less than a desired average coated API particle size. In some embodiments, more than one mesh can be used to remove certain particles. For example, a sieving device may comprise a series of two or more meshes to remove particles of a certain size according to the size of the mesh(s). The sieve can incorporate a vacuum transfer system to deliver the particles to the series of meshes of the device. Additionally, ultrasonic probes may be incorporated into the sieving device to improve material flow and minimize blinding of the mesh during processing. A flow aid (e.g., silica) may be included to promote movement through the sieve. For example, the coating material used to coat the API particles may comprise a flow aid. Conversely, raw API material may not be cohesive and not require the assistance of a flow aid during sieving. The sieving process may be a batch process or a continuous process.

In some embodiments, the raw API particles can be sieved using a mesh size from 30 µm to 500 µm, from 50 µm to 450 µm, from 100 µm to 400 µm, from 150 µm to 350 µm, or from 200 µm to 300 µm. In some embodiments, the raw API particles can be sieved using a mesh size less than 500 µm, less than 450 µm, less than 400 µm, less than 350 µm, less than 300 µm, less than 250 µm, less than 200 µm, less than 150, or less than 100 µm. In some embodiments, the raw API particles can be sieved using a mesh size greater than 30 µm, greater than 50 µm, greater than 100 µm, greater than 150 µm, greater than 200 µm, greater than 250 µm, greater than 300 µm, greater than 350 µm, or greater than 400 µm.

Once sieved, the coated API particles can be mixed into a matrix solution/suspension to form a pharmaceutical suspension and dosed by weight into pockets of preformed blister packs to form aliquots of pharmaceutical suspension. Once dosed, the blister packs with aliquots pharmaceutical suspension are frozen under sub-zero conditions. The frozen aliquots of pharmaceutical suspension is held frozen until it is ready for freeze drying during which the solvent of the pharmaceutical suspension is removed to form the pharmaceutical composition.

The matrix solution/suspension may include a matrix former, a structure former, and a solvent. For example, the matrix former may include any water soluble or water dispersable material that is pharmacologically acceptable or inert to the functionally-coated API particles. In some embodiments, the matrix former may be a polypeptide such as gelatin. The gelatin may be at least partially hydrolyzed (by heating in water). Other suitable matrix former materials include, but are not limited to, polysaccharides such as hydrolyzed dextran, dextrin, and alginates, polyvinyl alcohol, polyvinylpyrrolidone, and/or acacia. In some embodiments, the amount of matrix in a final pharmaceutical composition (e.g., an orally disintegrating tablet) may be 1-30% w/w. In some embodiments, the amount of matrix may be less than 30% w/w, less than 25% w/w, less than 20% w/w, less than 15% w/w, less than 10% w/w, less than 5% w/w, or less than 3% w/w. In some embodiments, the amount of matrix may be more than 1% w/w, more than 3% w/w, more than 5% w/w, more than 10% w/w, more than 15% w/w, more than % w/w, or more than 25% w/w.

In some embodiments, the amount of matrix former in a matrix solution/suspension or pharmaceutical suspension can be from about 0.1 to 10% w/w. In some embodiments, the amount of matrix former in the matrix solution/suspension or pharmaceutical suspension may include from 1.0 to 8.0% w/w or from 2.0 to 5.0% w/w. In some embodiments, the amount of matrix former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of matrix former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of matrix former in a pharmaceutical composition can be about 3-15% w/w, about 4-10% w/w, or about 4-7% w/w. In some embodiments, the amount of matrix former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than % w/w, more than 11.0% w/w, more than 12.0% w/w, more than 13.0% w/w, or more than 14.0% w/w. In some embodiments, the amount of matrix former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, less than 4.0% w/w.

A structure former, or bulking agent, of the matrix solution/suspension may include a sugar. For example, suitable structure formers include, but are not limited to, mannitol, dextrose, lactose, galactose, glycine, cyclodextrin, or combinations thereof. The structure former can be used in freeze drying as a bulking agent as it crystallizes to provide structural robustness to the freeze-dried dosage form. In some embodiments, the amount of structure former in the matrix solution/suspension can be from about 0.1 to 10% w/w. In some embodiments, the amount of structure former in the matrix solution/suspension or pharmaceutical suspension may include from 1.0 to 8.0% w/w or from 2.0 to 5.0% w/w. In some embodiments, the amount of structure former in the matrix solution/suspension or pharmaceutical suspension may include more than % w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of structure former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of structure former in a pharmaceutical composition can be about 3-15% w/w, about 4-10% w/w, or about 4-7% w/w. In some embodiments, the amount of structure former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than % w/w, more than 11.0% w/w, more than 12.0% w/w, more than 13.0% w/w, or more than 14.0% w/w. In some embodiments, the amount of structure former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

The solvent of the matrix solution/suspension and pharmaceutical suspension may be water, but the suspension solution may include a cosolvent as well. In some embodiments, the solvent can be ethanol, alcohol, isopropanol, other lower alkanols, water (e.g., purified water), or combinations thereof. For example, a suitable solvent and/or cosolvent may be an alcohol, such as tert-butyl alcohol. In some embodiments, the balance remaining of the pharmaceutical suspension is the solvent (i.e., Q.S. 100%).

The matrix solution/suspension and pharmaceutical suspension may also contain additional pharmaceutically acceptable agents or excipients. Such additional pharmaceutically acceptable agents or excipients include, without limitation, sugars, inorganic salts, such as sodium chloride and aluminum silicates, modified starches, preservatives, antioxidants, viscosity enhancers, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include aspartame, acesulfame K and thaumatin, and combinations thereof. Suitable taste-masking agents can include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

Figure 4:
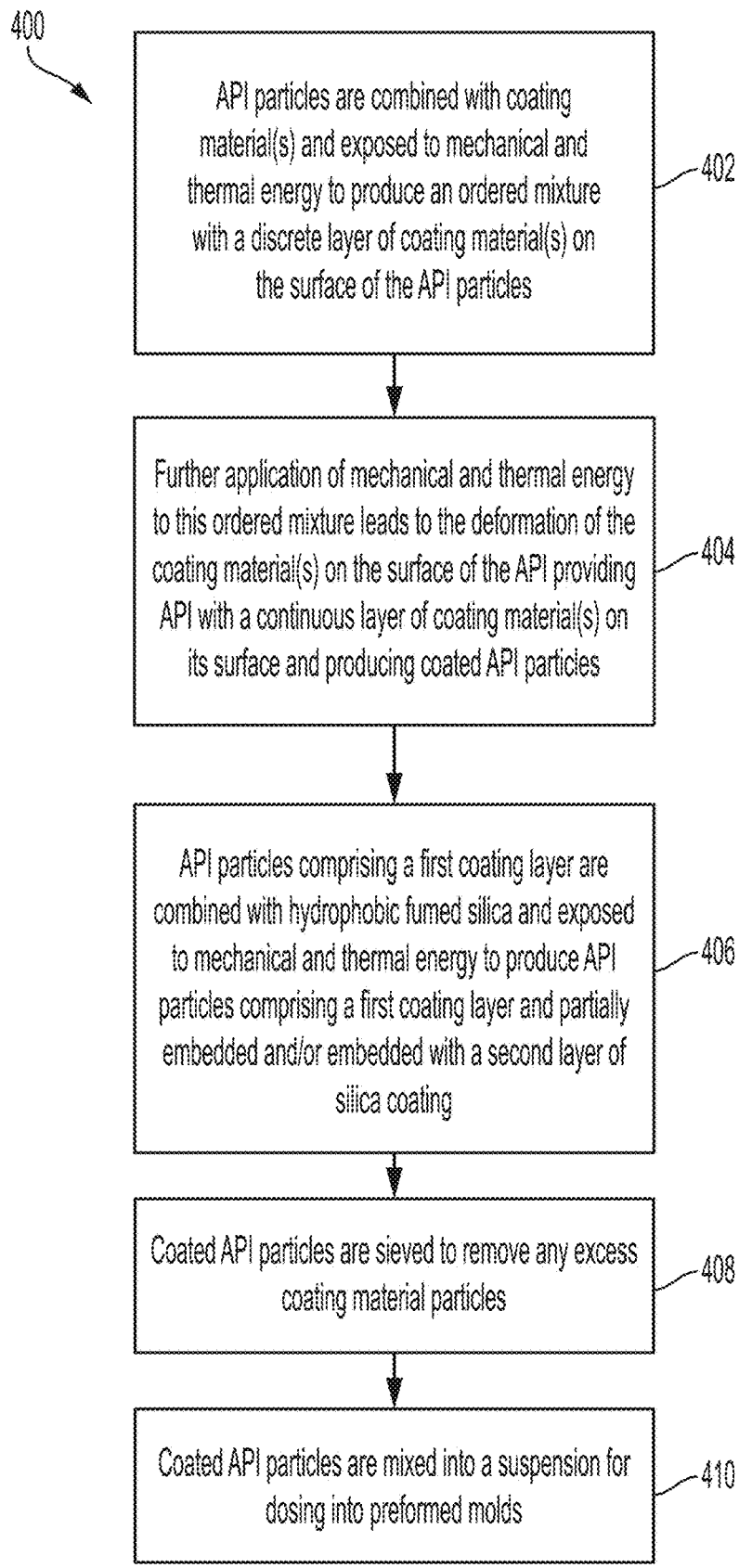
FIG. 4 is a flow chart of a mixing process for preparing coated API particles, according to some embodiments.

FIG. 4 provides a flow chart according to some embodiments of a mixing process for preparing pharmaceutical compositions described herein. In step 402, API particles are combined with one or more coating material(s), and the combination is exposed to mechanical and/or thermal energy to produce an ordered mixture of API particles comprising a discrete layer of one or more coating material(s) (i.e., API particles comprising a first coating layer). For example, FIG. 1A demonstrates an API particle comprising a discrete layer of coating material particles.

In step 404, mechanical and/or thermal energy may be applied to the coated API particles to deform one or more deformable components of the coating material to the surface of the API particle. This process step can form API particles comprising a continuous film surrounding the API particles. This is shown in FIG. 1B, FIG. 1C, and/or FIG. 3.

In step 406, coated API particles are combined with silica to form coated API particles comprising at least a first coating of functional coating material and a second coating of silica. In some embodiments, mechanical and/or thermal energy may be applied to cause the silica particles to adhere to and/or embed into the first coat of the coated API particles.

In step 408, coated API particles are sieved to remove any excess coating materials as discussed in detail above. For example, FIG. 3 shows an SEM image of coated API particle 312 and excess coating material 314.

In step 410, the sieved coated API particles are mixed into a matrix solution/suspension to form a pharmaceutical suspension for dosing into preformed molds. In some embodiments, the pharmaceutical suspension may be dosed into blister packs, freeze-dried to remove the solvent to form pharmaceutical compositions, and sealed in the blister packs for protection. This suspension and dosing process is covered in detail in GB 1548022, U.S. Pat. Nos. 4,371,516, 4,305,502, GB 211423, and U.S. Pat. No. 4,758,598, each of which is incorporated herein in its entirety.

The coating ratio (i.e., the amount of coating materials to the amount of uncoated API) may be optimized to minimize and/or prevent the agglomeration of the excess coating materials. For example, in some embodiments, the coating ratio can ranges from 5-85% or 10-150% w/w coating materials to 15-95% or 50-90% w/w uncoated API. In some embodiments, the amount of coating materials may be less than 80% w/w, less than 70% w/w, less than 60% w/w, less than 50% w/w, less than 40% w/w, less than 30% w/w, less than 20% w/w, or less than 10% w/w. In some embodiments, the amount of coating materials may be more than 5% w/w, more than 10% w/w, more than 20% w/w, more than 30% w/w, more than 40% w/w, more than 50% w/w, more than 60% w/w, or more than 70% w/w. In some embodiments, the amount of uncoated API may be less than 95% w/w, less than 85% w/w, less than 75% w/w, less than 65% w/w, less than 55% w/w, less than 45% w/w, less than 35% w/w, or less than 25% w/w. In some embodiments, the amount of uncoated API may be more than 20% w/w, more than 30% w/w, more than 40% w/w, more than 50% w/w, more than 60% w/w, more than 70% w/w, more than 80% w/w, or more than 90% w/w.

The dosing ratio (i.e., the amount of coated API to the amount of matrix solution/suspension comprising all the inactive ingredients) may be optimized to minimize and/or prevent the agglomeration of the excess coating materials. For example, in some embodiments, the dosing ratio can range from 5-60% w/w coated API to 40-95% w/w matrix solution/suspension In some embodiments, the dosing ratio may include less than 60% w/w, less than 50% w/w, less than 40% w/w, less than 30% w/w, less than 20% w/w, or less than 10% w/w coated API. In some embodiments, the dosing ratio may include more than 5% w/w, more than 10% w/w, more than 20% w/w, more than 30% w/w, more than 40% w/w, or more than 50% w/w coated API. In some embodiments, the dosing ratio may include less than 95% w/w, less than 90% w/w, less than 80% w/w, less than 70% w/w, less than 60% w/w, or less than 50% w/w matrix solution/suspension. In some embodiments, the dosing ration may include more than 40% w/w, more than 50% w/w, more than 60% w/w, more than 70% w/w, more than 80% w/w, or more than 90% w/w matrix solution/suspension.

EXAMPLES

Several trials were performed to evaluate the effectiveness of removing excess coating material from coated API particles by sieving and to optimize the coating ratios and dosing ratios. Disintegration times of pharmaceutical compositions containing various coated API particles were measured under various conditions to study the effect of sieving excess coating material. It may be reasonably assumed that removing excess coating material can minimize agglomeration of the coating material. Optimizing the coating and dosing ratios can also aid in minimizing coating material agglomeration. In turn, minimizing the amount of agglomeration can help maintain desired disintegration times and/or dissolution rates of the pharmaceutical composition and coated API particles. Accordingly, disintegration time is used as a metric to evaluate the amount of agglomeration in the following Examples. In some embodiments, the accelerated disintegration data can be indicative of the presence of unsieved, excess coating material.

Additionally, coating ratio and dosing ratio information is provided for the Examples below. Coating ratio refers to the amount of coating materials to the amount of uncoated API. Dosing ratio refers to the amount of coated API to the matrix solution/suspension comprising of all the inactive ingredients Example 1: Ibuprofen was coated with carnauba wax with a coating ratio of 26:74. A dosing ratio of 40:60 was used to produce freeze dried tablets. Four separate batches of tablets were tested—Batch 1-3 over a period of 2 months, and Batch 4 over a period of 6 months. These batches of tablets were each tested at ICH (International Council for Harmonisation of Technical Requirements for Pharmaceuticals for Human Use) stability conditions of 25° C./60% RH, RH, and 40° C./75% RH and sampled at one month and two months for Batches 1, 2, and 3. Additionally, each batch was exposed to a 50° C. stress condition to provide accelerated data at both two weeks and at four weeks for each study. Table 1 below provides the disintegration time data for Batches 1-3 of the two-month study of coated ibuprofen.

TABLE 1

| | | | | | | | 1 Month | 1 Month | 1 Month | 2 Month | 2 Month | 2 Month |
|---|---|---|---|---|---|---|---|---|---|---|---|---|
| | | | Initial | 2 Week | 4 Week | 25° C./ | 30° C./ | 40° C./ | 25° C./ | 30° C./ | 40° C./ |
| Batch | Batch Nos | Strength | DT | 50° C. | 50° C. | 60% RH | 65% RH | 75% RH | 60% RH | 65% RH | 75% RH |
| 1 | Z3876/128 | 400 MG | <2 s | <4 s | <10 s | <4 s | <4 s | <4 s | <3 s | <4 s | <7 s |
| 2 | Z4630/97 | 50 MG | <2 s | <4 s | <7 s | <2 s | <2 s | <2 s | <2 s | <2 s | <15 s |
| 3 | Z4630/101 | 50 MG | <3 s | <3 s | <4 s | <1 s | <2 s | <3 s | <2 s | <2 s | <2 s |

Carnauba Wax (Dosing Ratio 40:60) (2-Month Study)

Figure 5A:
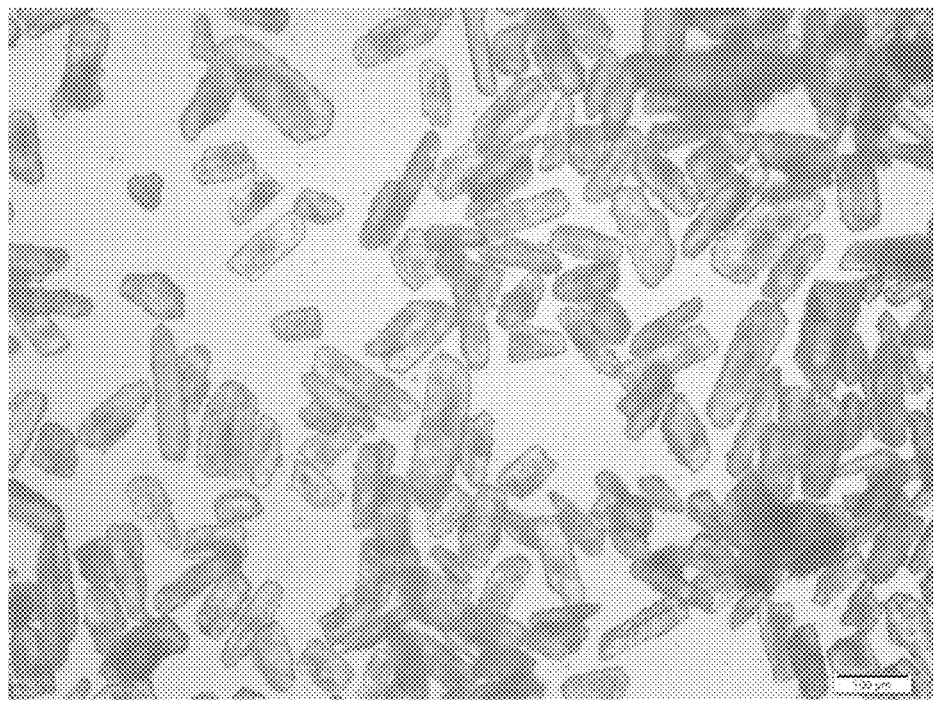
FIGS. 5A-5P are a series of photomicrographs taken of sieved coated API for Examples 1-8.
Figure 5B:
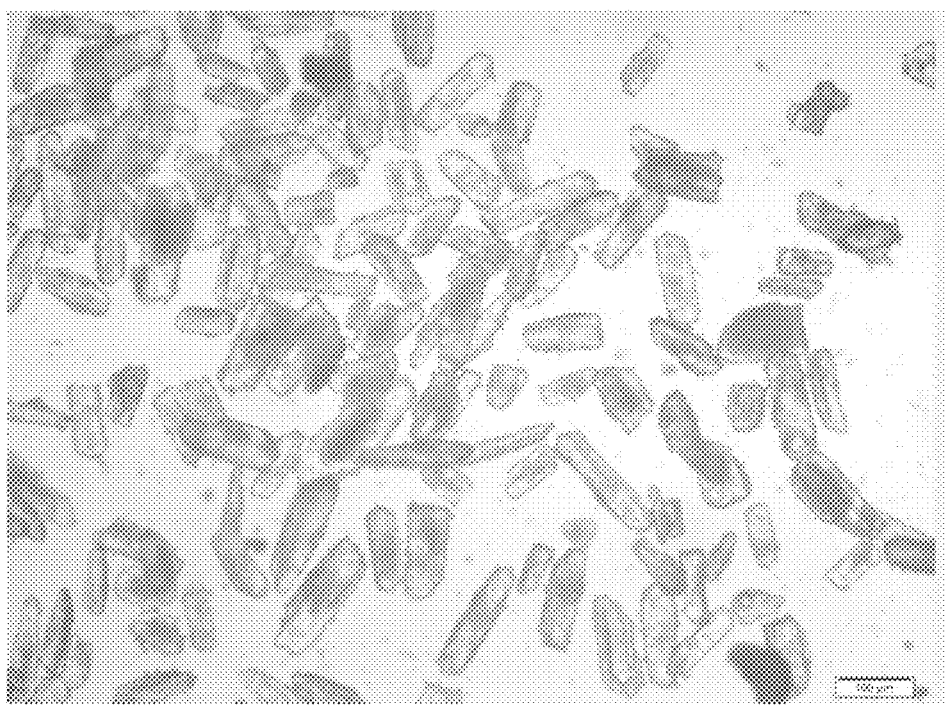

Coated API for Batch 2 was poorly sieved post API coating. Microscopic examination (FIG. 5B) of the sieved coated API showed the presence of an excess amount of unbound coating material. It also showed that the API particles were poorly coated. As shown in the last column of Table 1, this batch exhibited a significantly longer disintegration time at the RH stability testing conditions after two-months. (The initial disintegration time was less than two seconds, and the disintegration time at two months was almost 15 seconds). Accordingly, this result supports the hypothesis that the presence of an excess amount of unbound coating material in the pharmaceutical product is responsible for extended disintegration time over time (as the pharmaceutical product ages) because of the agglomeration of the unbound coating material during storage.

Figure 5C:
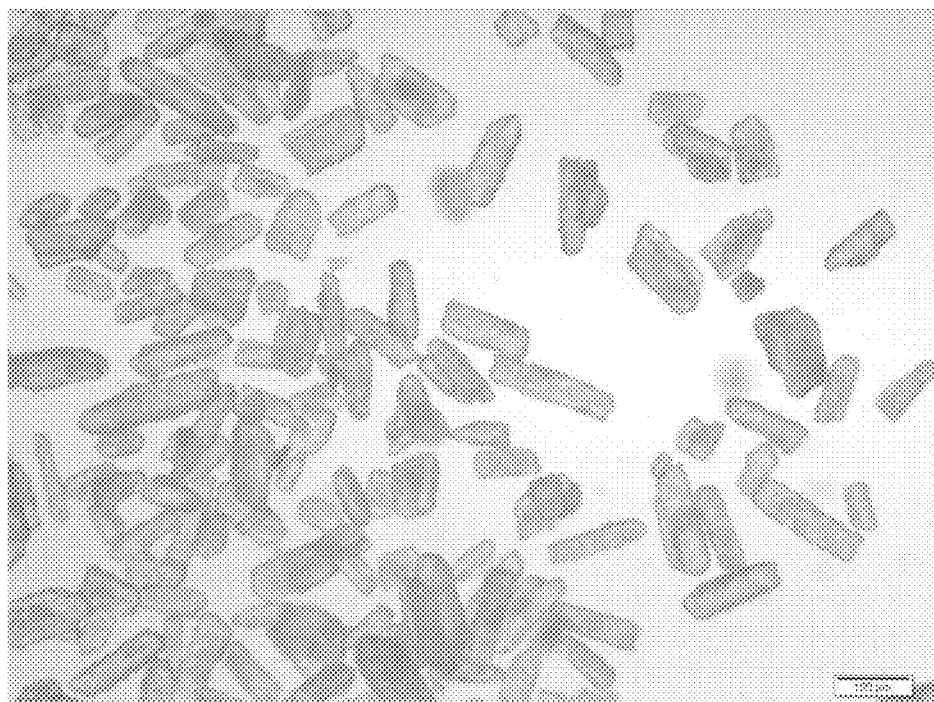

Conversely, coated API for Batch 3 was sieved well post-API coating. Microscopic examination (FIG. 5C) of the sieved coated API showed that the API particles were well coated since there is an absence of unbound coating material. The disintegration time for the samples of this batch changed very little over the two-month period for any of the ICH stability conditions. (The disintegration time throughout the two-month study fluctuated between approximately one second and approximately three seconds). This supports the hypothesis that minimizing the presence of excess unbound coating material by sieving, for example, will help to prevent the agglomeration of coating material in pharmaceutical product when place on storage, particularly at higher temperatures over time.

The coated API for Batch 1 was sieved post API coating. Batch 1 exhibited similar disintegration time of less than 2 seconds compared to Batch 2 and 3 for the initial time data points. However, at the 40 C/75% RH stability testing conditions after two-months, the disintegration time increased to approximately 7 seconds or less. When stored for 4 weeks at the disintegration time increased to approximately 10 seconds or less. This suggests that the sieving process for this batch did not sufficiently remove the excess coating material, hence the presence of residual unbound coating material. Batch 2 experienced even more unbound coating material and agglomeration on storage to a greater extent than that of Batch 1. Microscopic examination (FIG. 5A) of the sieved coated API showed that the API particles were moderately well coated with residue amount of unbound coating material present Table 2 below shows the disintegration time data for the six-month study of coated ibuprofen API (i.e., Batch 4).

TABLE 2

Carnauba Wax (Dosing Ratio 40:60) (6-Month Study)

| | | | | | | 1 Month | 1 Month | 1 Month | 3 Month | 3 Month | 3 Month | 6 Month | 6 Month | 6 Month |
|---|---|---|---|---|---|---|---|---|---|---|---|---|---|---|
| | | | | 2 Week | 4 Week | 25° C./ 60% RH | 30° C./ 65% RH | 40° C./ 75% RH | 25° C./ 60% RH | 30° C./ 65% RH | 40° C./ 75% RH | 25° C./ 60% RH | 30° C./ 65% RH | 40° C./ 75% RH |
| Batch | Batch Nos | Strength | Initial | 50° C. | 50° C. | RH | RH | RH | RH | RH | RH | RH | RH | RH |
| 4 | Z3876/131 | 200 MG | <5 s | <20 s | <13 s | <5 s | <4 s | <5 s | <4 s | <3 s | <4 s | <2 s | <2 s | <2 s |

Figure 5D:
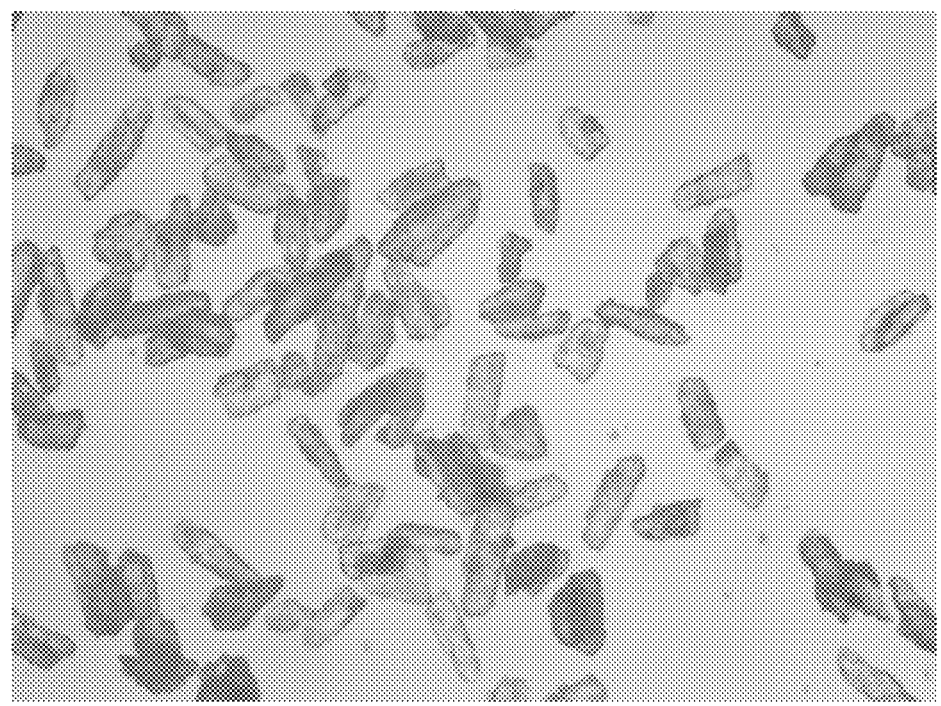

The coated API for Batch 4 was sieved post API coating. Batch 4 of Table 2 did not show much change in disintegration time throughout the duration of the six-month study. The initial disintegration time of Batch 4 was approximately five seconds, and the final disintegration time of the 25° C./60% RH samples was approximately two seconds; the 30° C./65% RH samples approximately two seconds, and the 40° C./75% RH samples approximately two seconds. However, an increase was seen when stored at 50° C. Since no increase was seen in the tablets stored at temperatures of 40° C. and below, this suggests that sieving has removed most of the unbound excess coating material but with sufficient residue amount that agglomerate when the tablets were placed at 50° C. Microscopic examination (FIG. 5D) showed that the sieved coated API showed that the API particles were moderately well coated with residue amount of unbound coating material present.

Figure 5E:
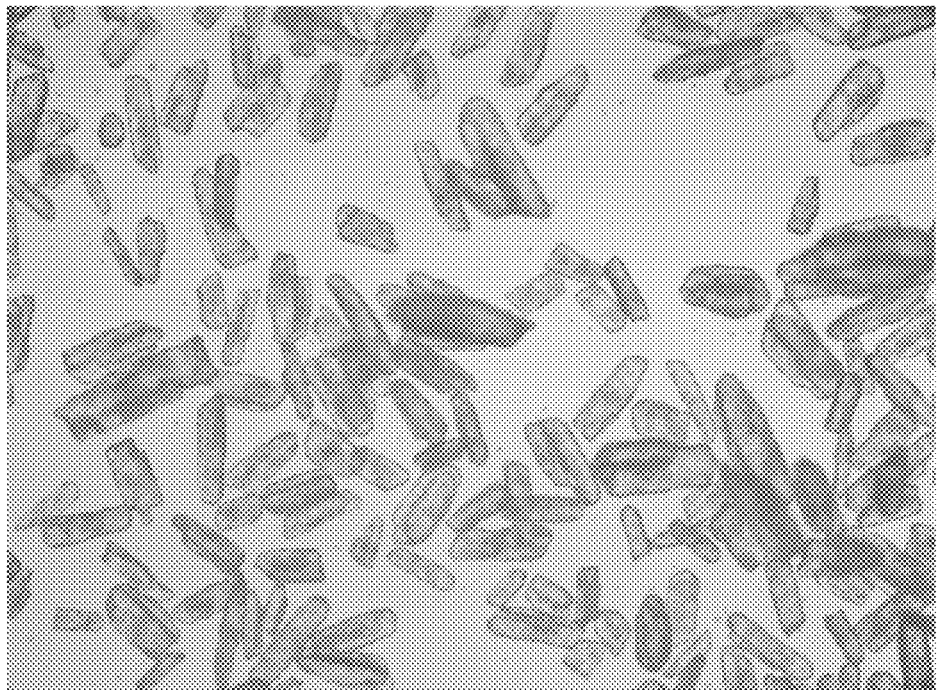

Example 2: Ibuprofen was coated with Sasol (synthetic) wax with a theoretical coating ratio of 26:74. The coated API was sieved after coating. A dosing ratio of 40:60 was used to produce freeze dried tablets and tested over two months. The ibuprofen API strength was 200 mg. Each batch was tested at ICH stability conditions of 25° C./60% RH, 30° C./65% RH, and 40° C./75% RH. Additionally, the samples were exposed to a 50° C. stress condition to provide accelerated data at two weeks and at four weeks during the study. Table 3 below provides the disintegration time data for the 40:60 dosing ratio two month study of coated ibuprofen. Microscopic examination (FIG. 5E) of the sieved coated API showed that the API particles were moderately well coated with a small amount of unbound coating material.

TABLE 3

Sasol Wax (Dosing Ratio 40:60) Ibuprofen Strength:200 mg

| Batch | Batch Nps | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|
| 5 | Z3876/138 | <3 s | <3 s | <4 s | <2 s | <2 s | <5 s | <4 s | <4 s | <4 s |

Batch 5 of Table 3 shows no substantial change in the disintegration time during the two months of the study, nor at the 50° C. accelerated conditions. Specifically, the initial disintegration time of Batch 5 was approximately three seconds, and the disintegration time at two months for all three ICH stability conditions (25° C./60% RH, 30° C./65% RH, and 40° C./75% RH) was approximately four seconds. The disintegration time for the 50° C. accelerated condition at two weeks was approximately three seconds and at 4 weeks was approximately four seconds. Based on the 50° C. data, a small residue amount of unbound excess coating material may be present. If so, this small amount of unbound excess coating material does not cause a significant amount of agglomeration on storage, since the disintegration time does not increase much, if at all. This compares well with Batch 3 in Example 1 where a different wax was used. These 2 examples demonstrate that if the unbound excess coating material is efficiency removed by sieving, agglomeration of the coating material in the pharmaceutical product on storage can be minimized or prevented, in particular at higher temperatures and upon prolonged storage period.

Figure 5F:
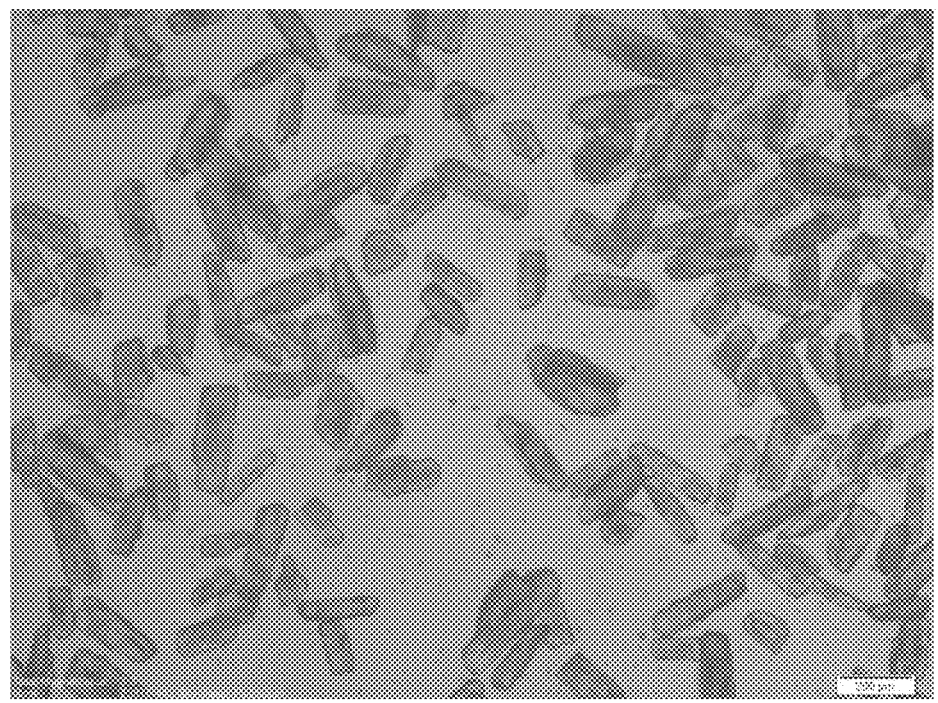

Example 3: Ibuprofen was coated with Sasol (synthetic) wax with a theoretical coating ratio of 26:74. The coated API was then sieved after coating. A dosing ratio of 50:50 was used to produce freeze dried tablets and tested over three months. The ibuprofen strength was 200 mg. As above in Examples 1 and 2, each batch was tested at ICH stability conditions of 25° C./60% RH, 30° C./65% RH, and 40° C./75% RH. The samples were also exposed to a 50° C. stress condition to provide accelerated data at two weeks and at four weeks during each study. Table 4, below, provides data for the three-month study of 50:50 Sasol wax-coated ibuprofen. Microscopic examination (FIG. 5F) of the sieved coated API for Batch 6 showed the API particles were coated well and with some unbound coating material.

month disintegration time for each of the three ICH stability conditions (25° C./60% RH, 30° C./65% RH, and 40° C./75% RH) was approximately two seconds. The disintegration time for both the two-week and the four-week accelerated 50° C. condition for Batch 6 was approximately two seconds.

The initial disintegration time for the samples of Batch 7 was approximately two seconds, and the final three-month disintegration time for the 25° C./60% and 30° C./65% ICH stability conditions was approximately two seconds. The final three-month disintegration time for the 40° C./75% ICH stability condition was approximately three seconds. The disintegration time for both the two-week and the four-week accelerated 50° C. condition was approximately five seconds. A high coating ratio of 50:50 can increase the amount of excess unbound coating material when left unsieved. Although both batches used a higher dosing ratio of 50:50, which means a high loading of the coated API and any unbound excess coating material, these data inferred that the sieving process of the coated API has been effective in removing the unbound excess coating materials to minimize agglomeration.

Figure 5G:
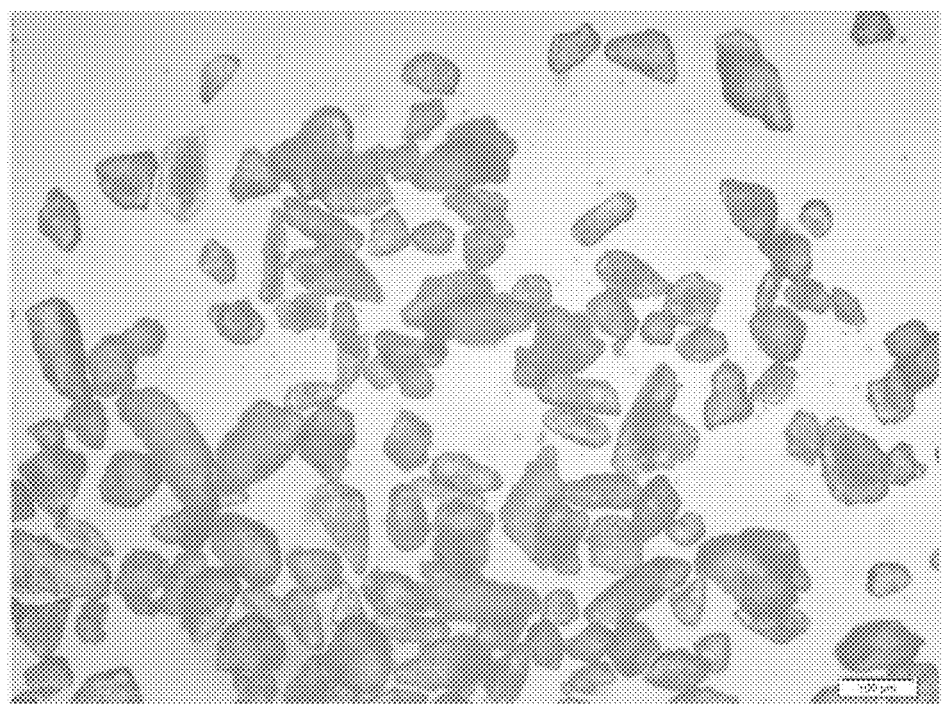

Example 4: Paracetamol (APAP) was coated with carnauba wax at a theoretical coating ratio of 26:74. For these batches, sieving was carried out manually. Dosing ratios of 50:50 and 40:60 were used to produce freeze dried tablets. The APAP strength was 325 mg. Each batch was tested at ICH stability conditions of 25° C./60% RH, 30° C./65% RH, and 40° C./75% RH. The samples were also exposed to a 50° C. stress condition to provide accelerated data at two weeks during each study. Table 5, below, provides data for the one-month study of carnauba wax-coated APAP. As shown below, all batches showed a significant increase in disintegration time for the 40° C./75% RH stability conditions at one month. Microscopic examination of the manually sieved coated API showed that for Batch 8 (FIG. 5G), the API particle coating was poor to moderate; for batches 9 and 10

TABLE 4

Sasol Wax (Dosing Ratio 50:50) Ibuprofen Strength:200 mg

| Batch | Batch Nos | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH | 3 Month 25° C./ 60% RH | 3 Month 30° C./ 65% RH | 3 Month 40° C./ 75% RH |
|---|---|---|---|---|---|---|---|---|---|---|---|---|---|
| 6 | Z3876/142 | <1 s | <2 s | <2 s | <2 s | <2 s | <2 s | <2 s | <1 s | <2 s | <2 s | <2 s | <2 s |
| 7 | Z3876/141/1 | <2 s | <5 s | <5 s | <2 s | <3 s | <3 s | <2 s | <2 s | <3 s | <2 s | <2 s | <3 s |

Figure 5H:
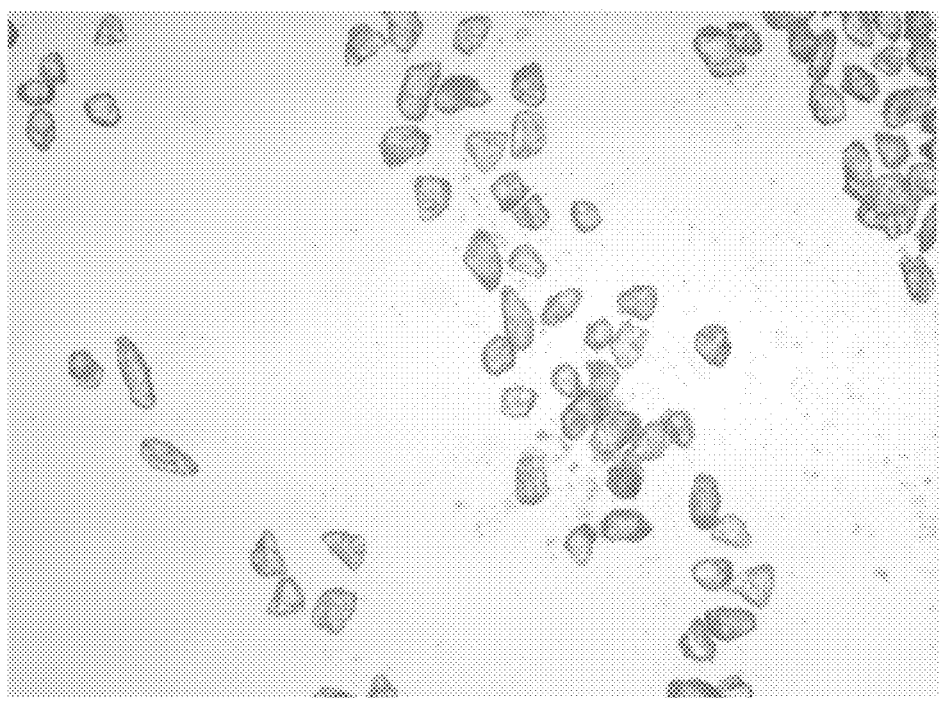
Figure 5I:
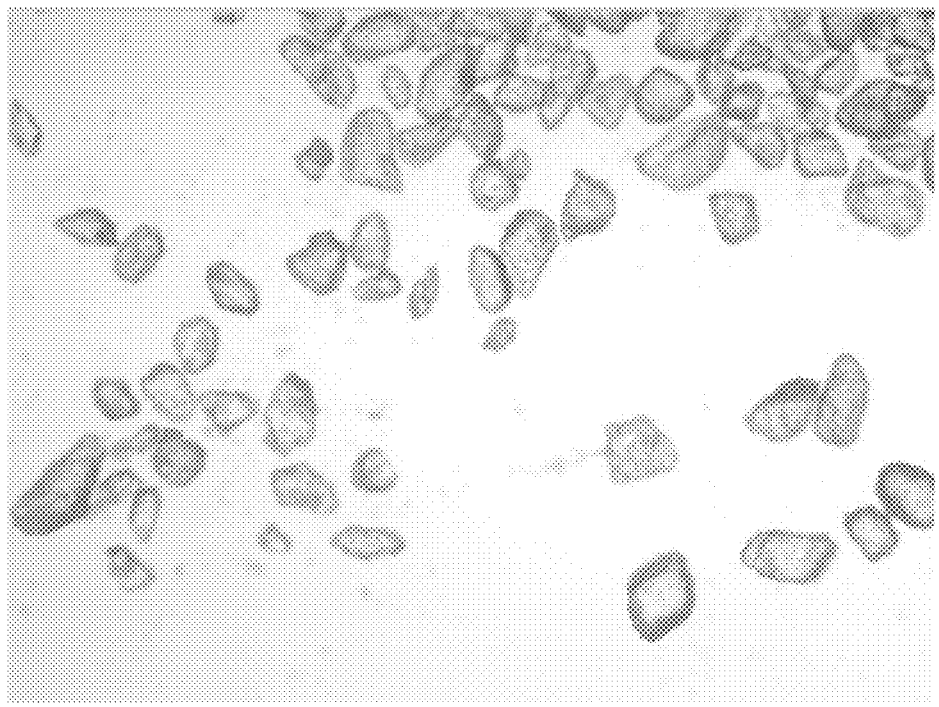

Neither Batch 6 nor Batch 7 showed significant change in disintegration time over the course of the three month study. Specifically, the initial disintegration time of the samples of Batch 6 was approximately one second, and the final three- (FIGS. 5H and 5I), the coating was very poor. Poor coating is due to the presence of the excess unbound coating material as a result of poor sieving which was carried out manually instead of using a sieve shaker.

TABLE 5

Carnauba Wax; APAP Strength:325 mg

| Batch | Batch Nps | Ratio | Initial DT | 2 Week 50° C. | 1 Month 25° C./ 60% RH | 1 Month 30° C./ 65% RH | 1 Month 40° C./ 75% RH |
|---|---|---|---|---|---|---|---|
| 8 | 33555J087 | 50:50 | <2 s | >2 mins | <3 s | <4 s | >2 mins |
| 9 | 3876/130/1 | 40:60 | <4 s | >2 mins | <3 s | <4 s | >2 mins |
| 10 | Z3876/130/2 | 40:60 | <3 s | >2 mins | <4 s | <3 s | >2 mins |

The initial disintegration time of the samples of each batch was approximately two to four seconds. None of the batches experienced much change in disintegration time for the 25° C./60% RH and 30° C./65% RH stability conditions when tested after one month. The disintegration time for all three batches at the two-week accelerated 50° C. condition was greater than two minutes. As mentioned above, all three batches also showed a significant increase in disintegration time after one month at the 40° C./75% RH stability condition—greater than two minutes. This can be explained by the presence of excess unbound wax coating materials, which agglomerated on storage of the pharmaceutical products.

Figure 5J:
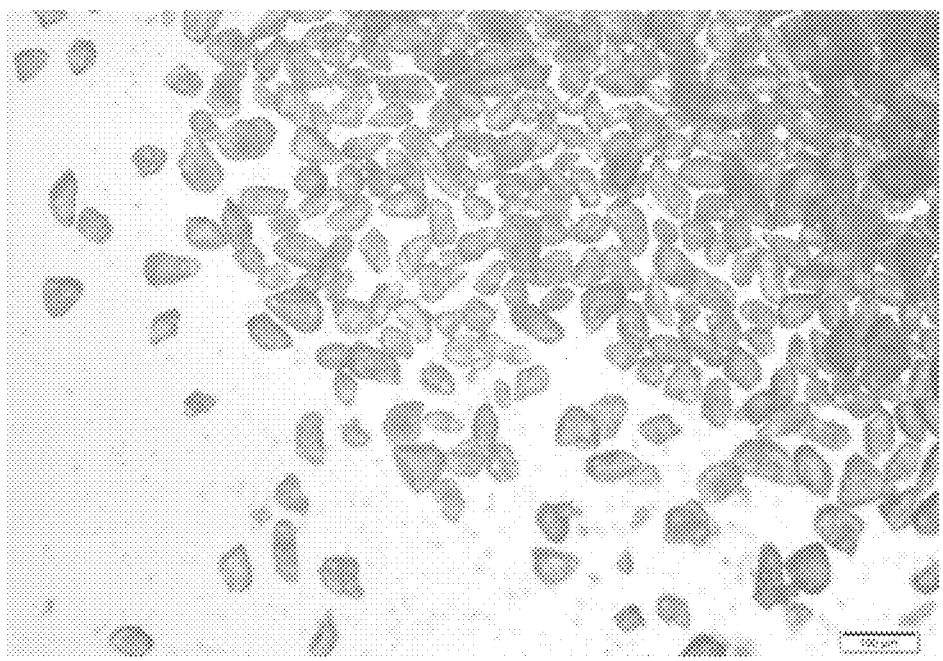

Example 5: APAP was coated with Sasol (synthetic) wax at a theoretical coating ratio of 26:74 and sieved. A dosing ratio of 50:50 to produce freeze dried tablets. The APAP strength was 325 mg. The testing conditions were identical to that described above in Example 4. Namely, the batch was tested at ICH stability conditions of 25° C./60% RH, 30° C./65% RH, and 40° C./75% RH. The sample was exposed to a 50° C. stress condition to provide accelerated data at two weeks. Table 6, below, provides data for the one-month study of Sasol (synthetic) wax-coated APAP. As shown below, Batch 11 did not show a significant change in disintegration time for any of the testing conditions. Microscopic examination (FIG. 5J) of the sieved coated API shows that the API particles were moderately well coated with unbound coating material present.

TABLE 6

Sasol Wax; APAP Strength:325 mg

| Batch | Batch Nos | Ratio | Initial DT | 2 Week 50° C. | 1 Month 25° C./ 60% RH | 1 Month 30° C./ 65% RH | 1 Month 40° C./ 75% RH |
|---|---|---|---|---|---|---|---|
| 11 | Z3876/129 | 50:50 | <2 s | >2 mins | <3 s | <4 s | <4 s |

The initial disintegration time of Batch 11 was less than two seconds. Little change in disintegration time occurred when tested at one month for all three stability conditions (25° C./60% RH, 30° C./65% RH, and 40° C./75% RH). The disintegration time at the two-week accelerated 50° C. condition was greater than two minutes. Since no increase was seen in the tablets stored at temperatures of 40° C. and below, this suggests that sieving has removed most of the unbound excess coating material but with sufficient residue amount that agglomerate when the tablets were placed at 50° C. Sasol wax also has a higher melting/softening point, which can occur at higher storage temperatures (e.g., 50° C.).

Figure 5K:
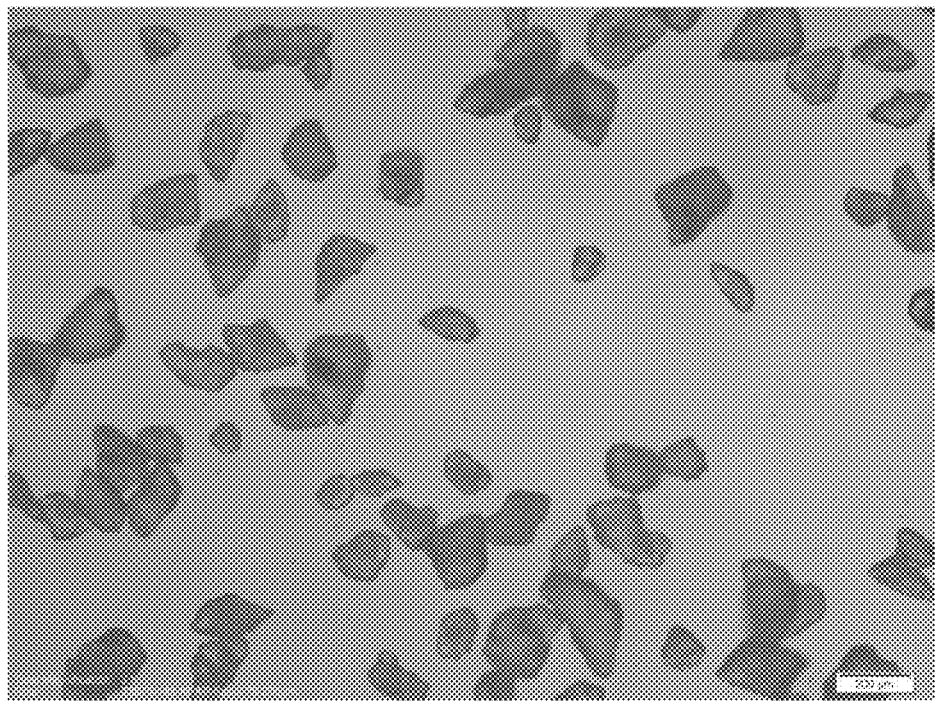

Example 6: APAP was coated with Sasol (synthetic) wax at a theoretical coating ratio of 24:76 and sieved. A dosing ratio of 50:50 was used to produce freeze dried tablets and studied over a period of three months and six months. (Batch 11 of Example 5 was extended from 1 month to 3 months for this example). The APAP strength for all samples was 325 mg. Each batch was tested at ICH stability conditions of 25° C./60% RH, 30° C./65% RH, and 40° C./75% RH. Additionally, the samples of each batch were exposed to a 50° C. stress condition to provide accelerated data at two weeks during each study. Table 7 below provides the disintegration time data for the 50:50 dosing ratio three month study (Batch 11) and six month study (Batch 12) of coated APAP. Similar to Batch 11, microscopic examination of the sieved coated API of Batch 12 (FIG. 5K) showed that the API particles were moderately well coated with unbound coating material.

TABLE 7

Sasol Wax (Dosing Ratio 50:50) APAP Strength:325 mg

| Batch | Batch Nps | Initial | 2 Week 50° C. | 1 Month 25° C./ 60% RH | 1 Month 30° C./ 65% RH | 1 Month 40° C./ 75% RH | 3 Month 25° C./ 60% RH | 3 Month 30° C./ 65% RH | 3 Month 40° C./ 75% RH | 6 Month 25° C./ 60% RH | 6 Month 30° C./ 65% RH | 6 Month 40° C./ 75% RH |
|---|---|---|---|---|---|---|---|---|---|---|---|---|
| 12 | Z3876/129 | <2 s | >2 min | <3 s | <4 s | <4 s | <4 s | <3 s | <3 s | N/A | N/A | N/A |
| 13 | Z3876/143 | <1 s | >2 min | <2 s | <2 s | <2 s | <2 s | <2 s | <3 s | <2 s | <2 s | <3 s |

Batch 12 showed no substantial change during the three month study of the 25° C./60% RH, 30° C./65% RH, and 40° C./75% RH ICH stability conditions. Specifically, the initial disintegration time was approximately two seconds, and the final three-month disintegration time for the 25° C./60% RH samples was approximately four seconds, and the final disintegration time for the 30° C./65% RH and 40° C./75% RH samples was approximately three seconds. However, the two-week 50° C. accelerated data exhibited a significant change in disintegration time (greater than two minutes). As noted in Example 5, Sasal Wax has a higher melting/softening temperature. Since no increase was seen in the tablets stored at temperatures of 40° C. and below, this relatively high melting/softening point supports the microscopic observation that the excess unbound coating material agglomerated when stored at 50° C. but did not agglomerate to the same extent when the tablets were stored at 40° C./75% RH.

Batch 13 behaved similarly to Batch 12 and showed no substantial change in disintegration time over the course of the six-month study. The initial disintegration time for the samples of Batch 13 was approximately one second. The final disintegration time at six months for the 25° C./60% RH and 30° C./65% RH samples was approximately two seconds, and the final disintegration time at six months for the 40° C./75% RH samples was approximately three seconds. Additionally, the two-week 50° C. accelerated data yielded a disintegration time of greater than two minutes.

Comparing the observation of Batches 12 and 13 with Batches 5-7 of Examples 3 and 4, both examples showed similar disintegration times for samples stored at 25° C./60%, 30° C./65% and 40° C./75%. However, a difference in disintegration time was observed for samples stored at After storing the tablets for 2 weeks at 50° C., for Batches 12 and 13, the disintegration times was greater than 2 minutes. In contrast, the disintegration times was 2-4 seconds. This difference suggests that there was a lesser amount of excess unbound coating material in Batches when compared with Batches 11-12. While this difference did not cause the agglomeration of the coating material at lower storage temperature of 25° C., 30° C. and 40° C., it is sufficient to make a difference at 50° C. due to the higher melting/softening temperatures of Sasol Wax.

Figure 5L:
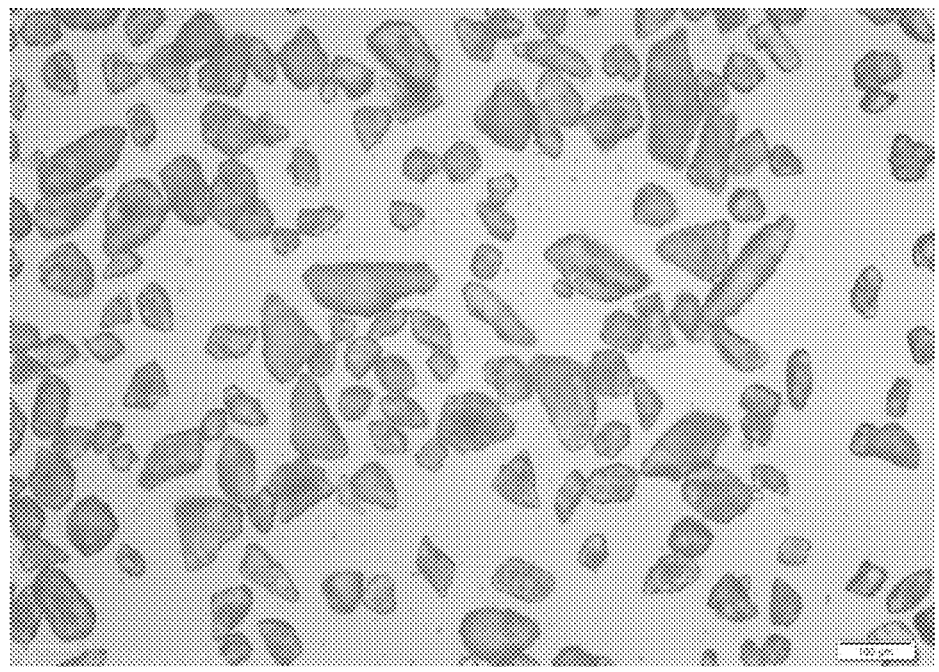

Example 7: APAP was coated with Sasol (synthetic) wax at a theoretical coating ratio of 26:74 and sieved. A dosing ratio of 40:60 to produce freeze dried tablets and studied over a period of two months. The APAP strength for all samples was 325 mg. The samples were tested at ICH stability conditions of 25° C./60% RH, 30° C./65% RH, and 40° C./75% RH. Additionally, the samples of each batch were exposed to a 50° C. stress condition to provide accelerated data at two weeks and four weeks during the study. Table 8 below provides the disintegration time data for this study. Similar to Batches 12 and 13, microscopic examination of the sieved coated API of Batch 14 (FIG. 5L) showed that the API particles were moderately well coated with a residue amount of unbound coating material.

TABLE 8

Sasol Wax (Dosing Ratio 40:60) APAP Strength:325 mg

| Batch | Bach Nps | Initial | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|
| 14 | Z3876/193 | <3 s | <3 s | <2 s | <2 s | <2 s | <3 s | <2 s | <2 s | <2 s |

Batch 14 showed no change in disintegration time over the course of the two-month study or in the accelerated data. The initial disintegration time of the samples of Batch 14 was approximately three seconds. The final two-month disintegration time for all three ICH stability conditions was approximately two seconds. Additionally, the two-week 50° C. accelerated data disintegration time was approximately three seconds, and the four-week 50° C. accelerated data disintegration time was approximately two seconds. Comparing this to Batch 11 from Example 5 and Batches 12 from Example 6 which used a dosing ratio of 50:50, this example shows that by reducing the dosing ratio to 40:60, it can reduce the amount of residual excess unbound coating material of the sieved coated API and minimize the agglomeration of the excess wax during storage, particularly at higher temperatures over time.

Figure 5M:
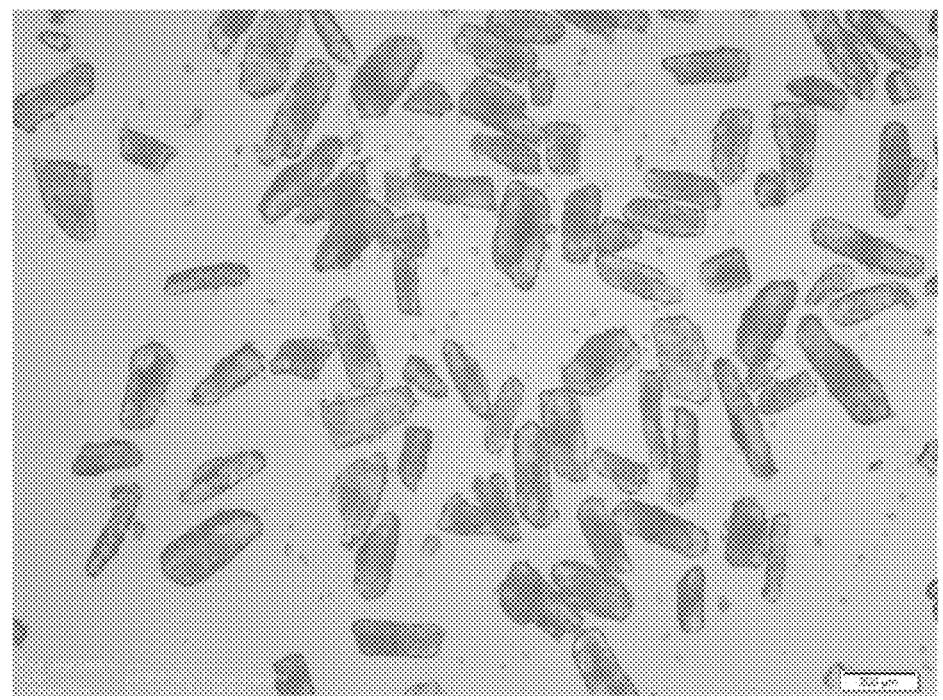
Figure 5N:
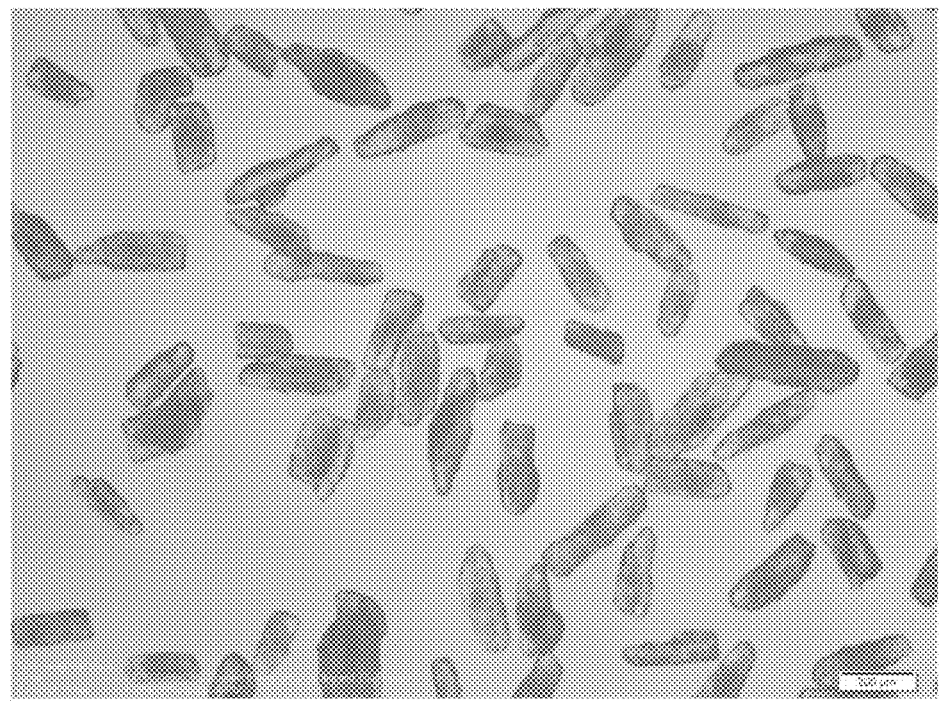
Figure 5O:
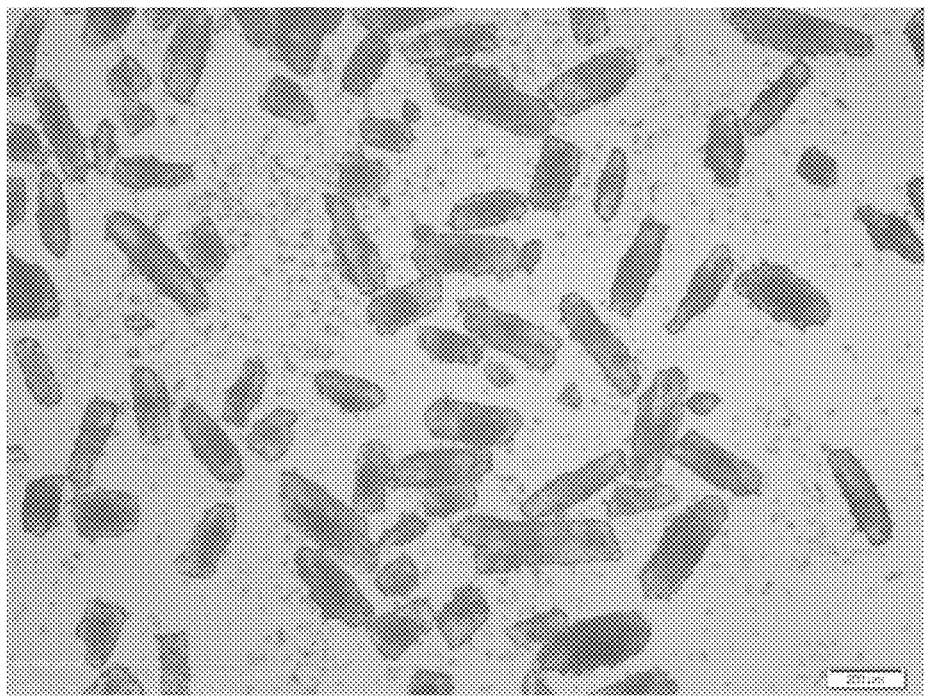
Figure 5P:
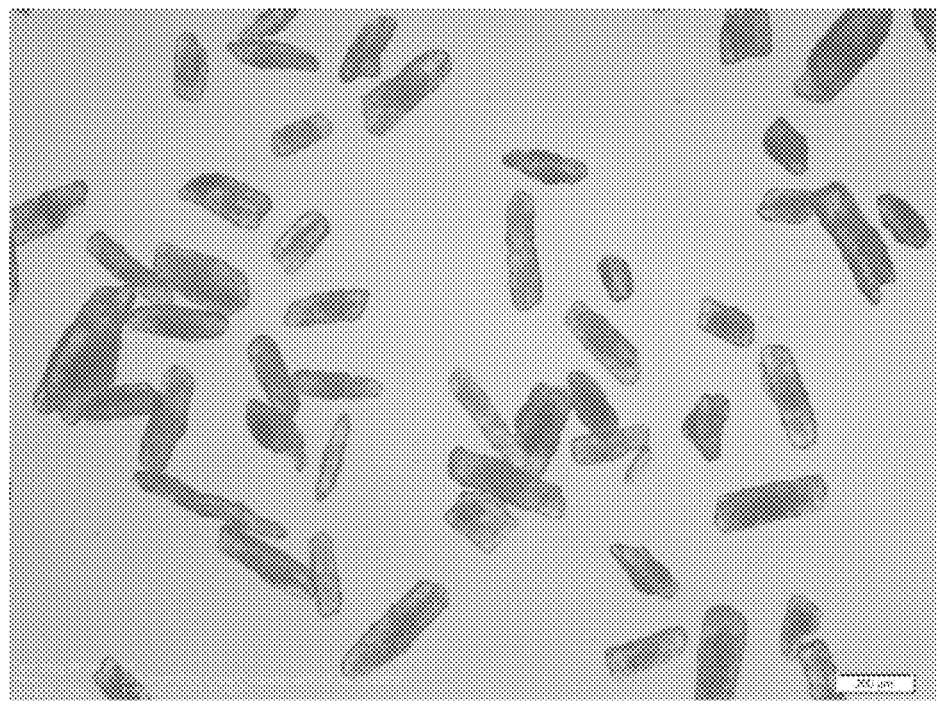

Example 8: Ibuprofen was coated with Carnuba Wax at a theoretical coating ratio of 22.5:77.5 and 30:70. A dosing ratio of 30:70 was used to produce freeze dried tablets and study over a period of 2 months. The Ibuprofen strength is 200 mg. The batches were stored in an oven at 40° C. Tablets were tested for disintegration time at the initial, Day 25, and 2 month time points. Table 9 below provides the disintegration times for the study. Microscopic examination of the unsieved coated API (FIGS. 5M and 5O) and sieved coated API (FIGS. 5N and 5P). The API particles were well coated. Sieved samples have no unbound coating material present.

TABLE 9

Carnuba Wax (Dosing Ratio 30:70) Ibuprofen Strength:200 mg

| Batch | Bach Nps | Coated API | Coating Ratio | Initial | Day 24 At 40° C. | 2 Month At 40° C. |
|---|---|---|---|---|---|---|
| 15 | Z4750/186/2a | Unsieved | 22.5:77.5 | 5 s | 2 s | 2 s |
| 16 | Z4750/186/4a | Sieved | 22.5:77.5 | 4 s | 3 s | 3 s |
| 17 | Z4750/186/6a | Unsieved | 30:70 | 1 s | 2 s | 2 s |
| 18 | Z4750/186/8a | Sieved | 30:70 | 2 s | 3 s | 3 s |

Batch 15-18 show that using a dosing ratio of 30:70 for coated API, either unsieved (Batches 15 and 17) or sieved (Batches 16 and 18), the disintegration times of the tablets stored at 40° C. not has increased over time. This supports the hypothesis that by reducing the dosing ratio; such as to 30:70, the amount of excess unbound wax is sufficiently reduced to a level that can minimize agglomeration of the excess unbound material when stored at higher temperatures over time.

The overall summary of results from the above examples are tabulated the Table 10

TABLE 10

Overall Summary of Results for Examples 1 to 8

| Batch | Batch Nos | Drug | Strength (mg) | Coating Ratio | Dosing Ratio | Sieving of Coated API | Coating Assessment (Microscopy) | Unbounded Excess Wax (Microscopy) | Disintegration Time at 40'C/75% RH at 1/2/3/6 mths | Disintegration time at 50'C at 2/4 wk |
|---|---|---|---|---|---|---|---|---|---|---|
| 1 | Z3876/128 | Ibuprofen | 400 | 26:74 | 40:60 | Sieved | Moderate | Present | <4-7 s | <4-10 s |
| 2 | Z4630/97 | Ibuprofen | 50 | 26:74 | 40:60 | Sieved (poor) | Poor | Present | <2-15 s | <4-7 s |
| 3 | Z4630/101 | Ibuprofen | 50 | 26:74 | 40:60 | Sieved (well) | Good | Absent | <2-3 s | <3-4 s |
| 4 | Z3876/131 | Ibuprofen | 200 | 26:74 | 40:60 | Sieved | Moderate | Present | <2-5 s | <13-20 s |
| 5 | Z3876/138 | Ibuprofen | 200 | 26:74 | 40:60 | Sieved | Good | Present | <4-5 s | <3-4 s |
| 6 | Z3876/142 | Ibuprofen | 200 | 26:74 | 50:50 | Sieved | Good | Present | <2 s | <2 s |
| 7 | Z3876/141/1 | Ibuprofen | 200 | 25:75 | 50:50 | Sieved | No Photo | No Photo | <3 s | <5 s |
| 8 | 33555J087 | APAP | 325 | 26:74 | 50:50 | Sieved (poor) | Poor to Moderate | Present | >2 mins | >2 mins |
| 9 | Z3876/130/1 | APAP | 325 | 26:74 | 40:60 | Sieved (poor) | Very Poor | Present | >2 mins | >2 mins |
| 10 | Z3876/130/2 | APAP | 325 | 26:74 | 40:60 | Sieved (poor) | Very Poor | Present | >2 mins | >2 mins |
| 11 | Z3876/129 | APAP | 325 | 26:74 | 50:50 | Sieved | Moderate | Present | <4 s | >2 mins |
| 11 | Z3876/129 | APAP | 325 | 26:74 | 50:50 | Sieved | Moderate | Present | <3-4 s | >2 min |
| 12 | Z3876/143 | APAP | 325 | 26:74 | 50:50 | Sieved | Moderate | Present | <2-3 s | >2 min |
| 13 | Z3876/139 | APAP | 325 | 26:74 | 40:60 | Sieved | Moderate | Present | <2-3 s | <2-3 s |
| 14 | Z4750/186/2a | Ibuprofen | 200 | 22.5:77.5 | 30:70 | Unsieved | Good | Present | <2 s | No data |
| 15 | Z4750/186/4a | Ibuprofen | 200 | 22.5:77.5 | 30:70 | Sieved (well) | Good | Absent | <3 s | No data |
| 16 | Z4750/186/6a | Ibuprofen | 200 | 30:70 | 30:70 | Unsieved | Good | Present | <2 s | No data |
| 17 | Z4750/186/8a | Ibuprofen | 200 | 30:70 | 30:70 | Sieved | Good | Absent | <3 s | No data |

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A pharmaceutical composition comprising:
65-85% w/w API particles;
15-30% w/w coating material encapsulating the API particles, wherein the coating material comprises wax and silica and the coated API particles comprise 0.5-5 wt. % silica; and
3-15% w/w matrix surrounding the coated API particles, wherein the pharmaceutical composition comprises a disintegration time of less than 10 seconds for at least six months under storage conditions of at least 25° C. and at least 60% relative humidity.

2. The pharmaceutical composition of claim 1, wherein the pharmaceutical composition comprises a disintegration time of less than 10 seconds for at least six months under storage conditions of at least 30° C. and at least 65% relative humidity.

3. The pharmaceutical composition of claim 1, wherein the pharmaceutical composition comprises a disintegration time of less than 10 seconds for at least six months under storage conditions of at least 40° C. and at least 75% relative humidity.

4. The pharmaceutical composition of claim 1, wherein the API particles comprise one or more of anti-inflammatories, analgesics, anti-psychotics, anti-emetics, laxatives, anti-diarrheals, anti-histamines, or anti-depressants.

5. The pharmaceutical composition of claim 1, wherein the wax comprises one or more of carnauba wax, candelilla wax, or synthetic wax.

6. The pharmaceutical composition of claim 1, wherein a coating ratio used to combine the API particles with the coating material comprises 5-85% w/w coating material and 15-95% w/w uncoated API particles.

7. The pharmaceutical composition of claim 1, wherein the matrix comprises a matrix former and a structure former.

8. The pharmaceutical composition of claim 7, wherein the matrix former comprises one or more of a water soluble material, a water dispersible material, a polypeptide, a polysaccharide, polyvinyl alcohol, polyvinylpyrrolidone, and acacia.

9. The pharmaceutical composition of claim 7, wherein the matrix former comprises a polypeptide.

10. The pharmaceutical composition of claim 8, wherein the polypeptide comprises gelatin.

11. The pharmaceutical composition of claim 6, wherein the structure former comprises one or more of mannitol, dextrose, lactose, galactose, and cyclodextrin.

12. The pharmaceutical composition of claim 6, wherein the structure former comprises mannitol.

13. The pharmaceutical composition of claim 1, wherein the silica produces a slower dissolution profile for the API as compared to API without silica.

14. The pharmaceutical composition of claim 13, wherein the coated API particles comprise 0.5-2.5 wt. % silica.

15. The pharmaceutical composition of claim 14, wherein the silica is partially embedded in and/or embedded in the wax.

\* \* \* \* \*